(12) United States Patent
Cohen et al.

(10) Patent No.: US 9,075,072 B2
(45) Date of Patent: Jul. 7, 2015

(54) MEANS AND METHODS FOR RECOGNIZING THE DEVELOPMENT OF CARDIOVASCULAR DISEASE IN AN INDIVIDUAL

(71) Applicant: YEDA RESEARCH & DEVELOPMENT CO. LTD., Rehovot (IL)

(72) Inventors: Irun R. Cohen, Rehovot (IL); Eytan Domany, Rehovot (IL); Eli Sahar, Tel Aviv (IL); Noam Shental, Rehovot (IL)

(73) Assignee: Yeda Research and Development Co. Ltd., Rehovot (IL)

(*) Notice: Subject to any disclaimer, the term of this patent is extended or adjusted under 35 U.S.C. 154(b) by 0 days.

(21) Appl. No.: 14/445,281

(22) Filed: Jul. 29, 2014

(65) Prior Publication Data
US 2014/0336077 A1 Nov. 13, 2014

Related U.S. Application Data

(63) Continuation of application No. 13/318,804, filed as application No. PCT/IL2010/000361 on May 5, 2010, now abandoned.

(60) Provisional application No. 61/175,472, filed on May 5, 2009.

(51) Int. Cl.
*G01N 33/53* (2006.01)
*G01N 33/68* (2006.01)
*G01N 33/564* (2006.01)

(52) U.S. Cl.
CPC .......... *G01N 33/6893* (2013.01); *G01N 33/564* (2013.01); *G01N 2500/04* (2013.01); *G01N 2800/324* (2013.01); *G01N 2333/47* (2013.01)

(58) Field of Classification Search
None
See application file for complete search history.

(56) References Cited

U.S. PATENT DOCUMENTS

| | | | |
|---|---|---|---|
| 5,545,534 A | 8/1996 | Akita | |
| 2002/0031788 A1* | 3/2002 | Rosenberg et al. | 435/7.21 |
| 2007/0218498 A1 | 9/2007 | Buechler | |
| 2009/0104201 A1 | 4/2009 | Smith | |
| 2011/0047632 A1* | 2/2011 | Robinson et al. | 800/9 |

FOREIGN PATENT DOCUMENTS

| | | |
|---|---|---|
| EP | 1722229 | 11/2006 |
| WO | 2004/025255 | 3/2004 |
| WO | 2007/085411 | 8/2007 |

OTHER PUBLICATIONS

Takamori et al. J. Neurological Science 1995 vol. 133, p. 95-101.*
Andraws et al., (2005) Effects of antibiotic therapy on outcomes of patients with coronary artery disease: a meta-analysis of randomized controlled trials. JAMA 293(21): 2641-7.
Andromeda Biotech Announces Successful Phase III Interim Results of Its Lead Product, DiaPep277 for Type 1 Diabetes. Medical News today, Jan. 2, 2009: http://www.medicalnewstoday.com/releases/134276.php.
Cohen (2002) Peptide therapy for Type I diabetes: the immunological homunculus and the rationale for vaccination. Diabetologia 45(10):1468-74.
Cohen (2007) Biomarkers, self-antigens and the immunological homunculus. J Autoimmun 29(4):246-9.
Cohen (2007) Real and artificial immune systems: computing the state of the body. Nat Rev Immunol 7(7): 569-74.
Cook et al., (2007) Long term effects of dietary sodium reduction on cardiovascular disease outcomes: observational follow-up of the trials of hypertension prevention (TOHP). BMJ 334(7599): 885-8.
Elias et al., (1990) Induction and therapy of autoimmune diabetes in the non-obese diabetic (NOD/LT) mouse by a 65-kDa heat shock protein. Proc Natl Acad Sci U S A 87(4): 1576-80.
Elias et al., (1991) Vaccination against autoimmune mouse diabetes with a T-cell epitope of the human 65-kDa heat shock protein. Proc Natl Acad Sci U S A 88(8): 3088-91.
Elliott et al., (1996) Intersalt revisited: further analyses of 24 hour sodium excretion and blood pressure within and across populations. Intersalt Cooperative Research Group. BMJ 312(7041): 1249-53.
Franco et al., (2004) the Polymeal: a more natural, safer, and probably tastier (than the Polypill) strategy to reduce cardiovascular disease by more than 75%. BMJ 329(7480): 1447-50.
Godlee F., Editor's Choice: Time to talk salt. Br Med J 2007; 334(7599):0. doi: 10.1136/bmj.39196.679537.47.
Grabar (1974) "Serand not-self" in immunology. Lancet 1(7870): 1320-2.
Huurman et al., (2008) Immunological efficacy of heat shock protein 60 peptide DiaPep277 therapy in clinical type I diabetes. Clin Exp Immunol 152(3): 488-97.
Jaffe (2006) Cardiovascular biomarkers: the state of the art in 2006. Clin Chim Acta 381(1):9-13.
May and Wang (2007) Evaluating the role of biomarkers for cardiovascular risk prediction: focus on CRP, BNP and urinary microalbumin. Expert Rev Mol Diagn 7(6): 793-804.
McGill et al., (2000) Associations of coronary heart disease risk factors with the intermediate lesion of atherosclerosis in youth. The Pathobiological Determinants of Atherosclerosis in Youth (PDAY) Research Group. Arterioscler Thromb Vasc Biol 20(8): 1998-2004.
Merbl et al., (2007) Newborn humans manifest autoantibodies to defined self molecules detected by antigen microarray informatics. J Clin Invest 117(3): 712-8.

(Continued)

*Primary Examiner* — Jacob Cheu
(74) *Attorney, Agent, or Firm* — Rodney J. Fuller; Booth Udall Fuller, PLC

(57) ABSTRACT

A method of recognizing the development of an Acute Myocardial Infarction (AMI) process in an individual, wherein the method comprises steps of: profiling specific antibody reactivities or biomarkers associated with AMI susceptibility, the profiling comprises steps of: attaching a set of defined antigens to a substrate; obtaining a biological fluid derived specimen from an individual, the specimen containing a specific antibody repertoire; and binding said antibodies of the biological fluid specimen to the attached antigens thereby forming bound antibody antigen complexes; and analyzing results obtained, wherein the presence of the complexes is indicative of AMI.

19 Claims, 8 Drawing Sheets

(56) References Cited

OTHER PUBLICATIONS

Miller et al., (2007) Use of BNP and CRP as biomarkers in assessing cardiovascular disease: diagnosis versus risk. Curr Vasc Pharmacol 5(1): 15-25.

Quintana et al., (2004) Functional immunomics: microarray analysis of IgG autoantibody repertoires predicts the future response of mice to induced diabetes. Proc Natl Acad Sci U S A 101 Suppl 2: 14615-21.

Quintana et al., (2006) Antigen-chip technology for accessing global information about the state of the body. Lupus 15 (7): 428-30.

Rainwater et al., (1999) Lipid and apolipoprotein predictors of atherosclerosis in youth: apolipoprotein concentrations do not materially improve prediction of arterial lesions in PDAY subjects. The PDAY Research Group. Arterioscler Thromb Vasc Biol 19(3): 753-61.

Raz et al., (2001) Beta-cell function in new-onset type 1 diabetes and immunomodulation with a heat-shock protein peptide (DiaPep277): a randomised, double-blind, phase II trial. Lancet 358(9295): 1749-53.

Real connection between oral health and heart disease University of Michigan Jan. 22, 1999.

Rosanoff and Seelig (2004) Comparison of mechanism and functional effects of magnesium and statin pharmaceuticals. J Am Coll Nutr 23(5): 501S-505S.

Studer et al., (2005) Effect of different antilipidemic agents and diets on mortality: a systematic review. Arch Intern Med 165(7): 725-30.

United States (1999). "Chronic Disease Overview". United States Government. Retrieved on Feb. 7, 2007.

Vanhecke et al., (2006) Awareness, knowledge, and perception of heart disease among adolescents. Eur J Cardiovasc Prey Rehabil 13(5): 718-23.

Vuilleumier et al., (2008) Anti-(apolipoprotein A-1) IgGs are associated with high levels of oxidized low-density lipoprotein in acute coronary syndrome. Clin Sci (Lond) 115(1): 25-33.

Wang et al., (2006) Multiple biomarkers for the prediction of first major cardiovascular events and death. N Engl J Med 355(25): 2631-9.

* cited by examiner

MEANS AND METHODS FOR RECOGNIZING THE DEVELOPMENT OF CARDIOVASCULAR DISEASE IN AN INDIVIDUAL

CROSS-REFERENCE TO RELATED APPLICATIONS

This patent application is a continuation of U.S. application Ser. No. 13/318,804, filed Nov. 4, 2011, which is the U.S. National Stage of International Application No. PCT/IL2010/000361, filed May 5, 2010, which claims the benefit of U.S. Provisional Application No. 61/175,472, filed May 5, 2009, the contents of each of which are herein incorporated by reference thereto in their entireties for all purposes.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 1,755 kilobyte ASCII (text) file named "Seq_List" created on Jul. 29, 2014.

FIELD OF THE INVENTION

The present invention pertains to methods of identifying the development of a cardiovascular disease in an individual. More specifically, the present invention discloses means and methods of recognizing the development of CVD, including an Acute Myocardial Infarction (AMI) process in an individual.

BACKGROUND OF THE INVENTION

Cardiovascular Disease

Cardiovascular disease refers to the class of diseases that involve the heart or blood vessels (arteries and veins). While the term technically refers to any disease that affects the cardiovascular system (as used in MeSH), it is usually used to refer to those related to atherosclerosis (arterial disease). These conditions have similar causes, mechanisms, and treatments. In practice, cardiovascular disease is treated by cardiologists, thoracic surgeons, vascular surgeons, neurologists, and interventional radiologists, depending on the organ system that is being treated. There is considerable overlap in the specialties, and it is common for certain procedures to be performed by different types of specialists in the same hospital.

Most Western countries face high and increasing rates of cardiovascular disease. Each year, heart disease kills more Americans than cancer [2]. Diseases of the heart alone caused 30% of all deaths, with other diseases of the cardiovascular system causing substantial further death and disability. Two out of three cardiac deaths occur without any diagnosis of cardiovascular disease [3]. Up until the year 2008, it was the major cause of death and disability in the United States and most European countries. A large histological study (PDAY) showed vascular injury accumulates from adolescence, making primary prevention efforts necessary from childhood [4] [5].

In contrast with gradual built-up of vessel narrowing, the major cause of heart attack (Acute Myocardial Infarction—AMI) or stroke is vulnerable (atherosclerotic) plaques. A vulnerable plaque is an athermatous plaque, an unstable collection of white blood cells (primarily macrophages) and lipids (including cholesterol) in the wall of an artery which is particularly prone to rupture, producing sudden vessel blockage and major problems, such as a heart attack. Researchers have found that inflammation in the arteries leads to the development of "soft" or vulnerable plaque, which when released aggressively promotes blood clotting. When this inflammation is combined with other stresses, such as high blood pressure (increased mechanical stretching and contraction of the arteries with each heart beat), it can cause the thin covering over the plaque to split, spilling the contents of the vulnerable plaque into the bloodstream. The sticky cytokines on the artery wall capture blood cells (mainly platelets) that accumulate at the site of injury. When these cells clump together, they form a clot, sometimes large enough to block the artery. The most frequent cause of a cardiac event following rupture of a vulnerable plaque is blood clotting on top of the site of the ruptured plaque that blocks the lumen of the artery, thereby stopping blood flow to the tissues the artery supplies.

By the time that heart problems are detected, the underlying cause (atherosclerosis) is usually quite advanced, having progressed for decades. There is therefore increased emphasis on preventing atherosclerosis by modifying risk factors, such as healthy eating, exercise and avoidance of smoking. Established cardiovascular risk factors, including dyslipidemia, smoking, hypertension, and diabetes mellitus, have been incorporated into algorithms for risk assessment in the general population [1], [2] but these characteristics do not fully explain cardiovascular risk [3], [4], [5] and other factors are sought.

Biomarkers

A biomarker is a substance or measurement that indicates important facts about a living organism, usually a patient. It is objectively measured and evaluated as an indicator of normal biologic processes, pathogenic processes, or pharmacologic responses to a therapeutic intervention. In other words, biomarkers can provide the physician with useful information about:

1. Biologic state of an individual;
2. Disease risk;
3. Disease diagnosis;
4. Disease progression;
5. Treatments of choice;
6. Monitoring responses to treatment;
7. Endpoints for assessing treatment efficacy.

Biomarkers thus allow the physician a preventive or therapeutic jump on the individual's disease process.

An effective biomarker, as a high concentration of "bad" cholesterol, for example, can inform us about associated complexities related to genes, heredity, metabolism, diet, blood vessel walls, and the risks of vascular embolism and occlusion [3]. The biomarker, in short, reflects and summarizes all the agents and processes that are needed to produce it—however many and complex these agents and processes may be. A simple biomarker is informative when it faithfully signifies for us the complex factors from which the biomarker emerges.

There is thus substantial interest in the use of newer biomarkers to identify persons who are at risk for the development of cardiovascular disease and who could be targeted for preventive measures. Some biomarkers are thought to offer a more detailed risk of cardiovascular disease. However, the clinical value of these biomarkers is questionable [6]. Many individual biomarkers have been related to cardiovascular risk in ambulatory persons, including levels of C-reactive protein [7], [8], B-type natriuretic peptide [9], fibrinogen [10], D-dimer [11] and homocysteine [12]. Measurement of several biomarkers simultaneously (the "multimarker" approach) could enhance risk stratification of ambulatory persons. This approach was tried by Wang et al. (NEJM v.355.2631-2639), by testing the usefulness of 10 previously reported biomarkers for predicting death and major cardiovascular events in a large population. However, the results were unpromising.

Currently, biomarkers which may reflect a higher risk of cardiovascular disease include:
  Higher fibrinogen and PAI-1 blood concentrations;
  Elevated homocysteine, or even upper half of normal;
  Elevated blood levels of asymmetric dimethylarginine;
  High inflammation as measured by C-reactive protein; and,
  Elevated blood levels of Brain Natriuretic Peptide (also known as B-type) (BNP) [7].

A fairly recent emphasis is on the link between low-grade inflammation that hallmarks atherosclerosis and its possible interventions. C-reactive protein (CRP) is an inflammatory marker that may be present in increased levels in the blood in patients at risk for cardiovascular disease. Its exact role in predicting disease is the subject of debate.

In light of the above, it is clear that a long felt and unmet need exists for a reliable method of identifying at a very early stage, the beginning of a cardiovascular disease in an individual. Such a method would make it possible to act quickly without having to wait for real-time events to take place. For example, anticipating, treating and monitoring the state of the individual would improve the ability to prevent a future heart attack or an impending stroke event.

SUMMARY OF THE INVENTION

It is hence one object of the present invention to provide a method of recognizing the development of an Acute Myocardial Infarction (AMI) process in an individual. The aforementioned method comprises steps of: profiling specific antibody reactivities or biomarkers associated with AMI susceptibility, and analysing results obtained. The profiling step further comprises steps of: (a) attaching a set of defined antigens to a substrate; (b) obtaining a biological fluid derived specimen from an individual, said specimen containing a specific antibody repertoire; and, (c) binding said antibodies of said biological fluid specimen to said attached antigens thereby forming bound antibody antigen complexes.

It is a further object of the present invention to disclose the method as defined above, wherein said profiling further comprises the steps of obtaining said defined antigens characterized by association with a variety of conditions selected from a group consisting of inflammation, angiogenesis, apoptosis or any other condition involving immune regulation or any combination thereof.

It is a further object of the present invention to disclose the method as defined above, wherein said profiling further comprising the steps of selecting said biological fluid derived specimen from a group consisting of plasma, serum, blood, cerebrospinal fluid, synovial fluid, sputum, saliva, tears, lymph specimen, or any other biological fluid known in the art.

It is a further object of the present invention to disclose the method as defined above, wherein said profiling further comprises steps of selecting said substrate from a group consisting of microarray chip, microarray wafers, microarray strips, ELISA microwells, multiplex beads or any substrate known in the relevant art.

It is a further object of the present invention to disclose the method as defined above, further comprising the steps of selecting said antigens from a group consisting of protein, polypeptide, peptide, nucleic acids, lipids, glycosylated molecules, polypeptides with modifications, polysaccharides or any other biological molecule known in the art.

It is a further object of the present invention to disclose the method as defined above, further comprising the steps of defining said antibody reactivities as IgG, IgM, IgA, IgE antibody isotypes or more specific sub-isotypes of said antibodies.

It is a further object of the present invention to disclose the method as defined above, wherein said analyzing results obtained further comprising the steps of measuring said bound antibody complexes.

It is a further object of the present invention to disclose the method as defined above, wherein said measuring additionally comprises steps of labeling said bound antibody complexes.

It is a further object of the present invention to disclose the method as defined above, wherein said labeling further comprises the steps of selecting a labeling signal from a group consisting of fluorescent, chemiluminescent, absorptive, electronic, radioactive, paramagnetic or any labeling signal known in the art, or combination thereof.

It is a further object of the present invention to disclose the method as defined above, wherein said labeling step additionally comprises steps of reacting said bound antibody complexes with labeled mixture of secondary antibodies specific for human immunoglobulin types so as to obtain labeled bound antibody antigen complexes.

It is a further object of the present invention to disclose the method as defined above, wherein said analyzing step additionally comprises steps of: (a) scanning the signal produced by said bound antibody complexes so as to form a reactivity matrix; (b) measuring the intensity of said signal; (c) generating and recording results of data associated with said intensity of said signal; (d) producing said results in the form of a signature, profile, set, pattern or matrix characteristic to said individual; (e) comparing the results with a databank containing data concerning said antibody reactivities in populations susceptible to AMI thereby identifying the development of an Acute Myocardial Infarction (AMI) process in said individual.

It is a further object of the present invention to disclose the method as defined above, wherein said measuring and scanning steps are selected from a group consisting of Surface Plasmon Resonance (SPR), ellipsometry, laser scanning, light detecting, photon detecting via a photon multiplier, photographing with a digital camera based system or video system, radiation counting, fluorescence detecting, electronic, magnetic detecting or any other technique known in the art or combination thereof.

It is a further object of the present invention to disclose the method as defined above, wherein said analyzing step further comprises the steps of defining said reactivity as a relative intensity signal of a specific bound antibody as compared to its intensity signal in healthy control individuals.

It is a further object of the present invention to disclose the method as defined above, wherein said analyzing step further comprises the steps of defining said reactivity as a relative intensity signal of a specific bound antibody as compared to its intensity signal in individuals who have had a stroke event.

It is a further object of the present invention to disclose the method as defined above, wherein said analyzing step further comprises the steps of identifying a set of informative antigens possessing higher or a lower intensity reactivity matrix signals as compared to said intensity signals of said antibodies in healthy control individuals.

It is a further object of the present invention to disclose the method as defined above, wherein said analyzing step further comprises the steps of identifying a set of informative antigens possessing higher or a lower intensity reactivity matrix signals as compared to said intensity signals of said antibodies in individuals who have had a stroke event.

It is a further object of the present invention to disclose the method as defined above, wherein said method further comprises steps of: (a) obtaining said antigens attached to said substrate; (b) packaging said substrate attached antigens in a kit containing instructions; and, (c) following the steps according to said instructions.

It is another core object of the invention to provide a set of informative antigens useful for recognizing the development of an Acute Myocardial Infarction (AMI) process in an individual. According to certain embodiments of the present invention, some of the herein disclosed informative antigens are specific peptides. The aforementioned set of antigens is selected from a group consisting of Brain-1 oligo-dendrocyte transcription factor, Synaptotagmin 1, Tryptophan hydroxylase peptide 1, Tryptophan hydroxylase peptide 2, BSP (Brain specific protein), myelin associated glycoprotein, Fibronectin, Caspase 3, Myelin-associated metalloproteinase, CD68, Bone morphogenic protein 4 and D4GDI (GDP-dissociation inhibitor). The aforementioned antibody reactivities are profiled by: profiling means for profiling specific antibody reactivities or biomarkers associated with AMI susceptibility, and analyzing means for analyzing results obtained. The aforementioned profiling means further comprising: (a) attaching means for attaching a set of defined antigens to a substrate; (b) a biological fluid derived specimen from an individual, said specimen containing a specific antibody repertoire; and, (c) binding means for binding said antibodies of said biological fluid specimen to said attached antigens thereby forming bound antibody antigen complexes.

It is a core aspect of the invention that the antigens are further characterised by their specific antibody reactivity with human antibodies associated with susceptibility to AMI.

Moreover, it is a core aspect of the present invention to provide means and methods to differentiate diagnoses of stroke and AMI. The finding that stroke and AMI differ in their antigen chip signature is highly novel, even though both conditions have been assumed to involve similar atherosclerotic processes. The diagnostic methods for stroke provided herein are particularly useful in differentiating from brain tumors for example, which may present with similar initial symptoms.

It is a further object of the present invention to disclose the set of informative antigens as defined above, wherein said defined antigens characterized by association with a variety of conditions selected from a group consisting of inflammation, angiogenesis, apoptosis or any other condition involving immune regulation or any combination thereof.

It is a further object of the present invention to disclose the set of informative antigens as defined above, wherein said defined antigens are attached to a substrate selected from a group consisting of microarray chip, microarray wafers, microarray strips, ELISA microwells, multiplex beads or any substrate known in the relevant art.

It is a further object of the present invention to disclose the set of informative antigens as defined above, wherein said defined antigens are selected form a group consisting of protein, polypeptide, peptide, nucleic acids, lipids, glycosylated molecules, polypeptides with modifications, polysaccharides or any other biological molecule known in the art.

It is a further object of the present invention to disclose the set of informative antigens as defined above, wherein said antigens are further characterized by their specific capability to discriminate between an individual harboring the development of an AMI process and a healthy control individual.

It is a further object of the present invention to disclose the set of informative antigens as defined above, wherein said antigens are further characterized by their specific capability to discriminate between the development of an AMI process and a stroke process in an individual.

It is a further object of the present invention to disclose the set of informative antigens as defined above, wherein said human antibodies are derived from a biological fluid specimen selected from a group consisting of plasma, serum, blood, cerebrospinal fluid, synovial fluid, sputum, saliva, tears, lymph specimen, or any biological fluid known in the art.

It is a further object of the present invention to disclose the set of informative antigens as defined above, wherein said antibody reactivities are defined as IgG, IgM, IgA, IgE antibody isotypes or more specific sub-isotypes of said antibodies.

It is a further object of the present invention to disclose the set of informative antigens as defined above, wherein said specific antibody reactivity is analyzable by using measuring means.

It is a further object of the present invention to disclose the set of informative antigens as defined above, wherein said specific antibody reactivity is analyzable by using labeling means.

It is a further object of the present invention to disclose the set of informative antigens as defined above, wherein said labeling means is adapted to label said human antibodies with a mixture of secondary antibodies specific for human immunoglobulin types to form a reactivity matrix.

It is a further object of the present invention to disclose the set of informative antigens as defined above, wherein said labeling means comprises labeling signal selected form a group consisting of fluorescent, chemiluminescent, absorptive, electronic, radioactive, paramagnetic or any labeling signal known in the art, or combination thereof.

It is a further object of the present invention to disclose the set of informative antigens as defined above, wherein said specific antibody reactivity is further analyzable by: (a) using a scanning means for scanning said reactivity matrix signal; (b) using a measuring means for measuring the intensity of said signal; (c) using generating and recording means for generating and recording results associated with said reactivity matrix signal; (d) using producing means for producing said results in the form of a signature, profile, set, pattern or matrix characteristic to said individual; and, (e) using means for comparing the results with a databank containing data concerning said antibody reactivities in populations susceptible to AMI, thereby identifying the development of an Acute Myocardial Infarction (AMI) process in said individual.

It is a further object of the present invention to disclose the set of informative antigens as defined above, wherein said measuring and scanning means are selected from a group consisting of Surface Plasmon Resonance (SPR), ellipsometry, laser scanning, light detecting, photon detecting via a photon multiplier, photographing with a digital camera based system or video system, radiation counting, fluorescence detecting, electronic, magnetic detecting or any other technique known in the art or combination thereof.

It is a further object of the present invention to disclose the set of informative antigens as defined above, wherein said reactivity is defined as a relative intensity of a specific antibody bound antigen as compared to its intensity signal in healthy control individuals.

It is a further object of the present invention to disclose the set of informative antigens as defined above, wherein said reactivity is defined as a relative intensity of a specific antibody bound antigen as compared to its intensity signal individuals who have had a stroke event.

It is a further object of the present invention to disclose the set of informative antigens as defined above, wherein said reactivity is further defined as a set of informative antigens possessing a higher or a lower intensity reactivity signals as compared to said intensity signals of said antigens in said healthy control individuals.

It is a further object of the present invention to disclose the set of informative antigens as defined above, wherein said reactivity is further defined as a set of informative antigens possessing a higher or a lower intensity reactivity signals as compared to said intensity signals of said antigens in individuals who have had a stroke event.

It is another core object of the invention to provide a reactivity matrix useful for recognizing the development of an Acute Myocardial Infarction (AMI) process in an individual, comprising at least one substrate embedded with defined antigens. According to certain embodiments of the present invention, some of the herein disclosed defined antigens are specific peptides. The aforementioned defined antigens are selected from a group consisting of Brain-1 oligo-dendrocyte transcription factor, Synaptotagmin 1, Tryptophan hydroxylase peptide 1, Tryptophan hydroxylase peptide 2, BSP (Brain specific protein), myelin associated glycoprotein, Fibronectin, Caspase 3, Myelin-associated metalloproteinase, CD68, Bone morphogenic protein 4 and D4GDI (GDP-dissociation inhibitor), wherein said antigens are further characterised by their specific antibody reactivity with human specimen containing antibodies associated with susceptibility to AMI.

It is a further object of the present invention to disclose the reactivity matrix as defined above, wherein said human antibodies are derived from a biological fluid specimen selected from a group consisting of plasma, serum, blood, cerebrospinal fluid, synovial fluid, sputum, saliva, tears, lymph specimen, or any biological fluid known in the art.

It is a further object of the present invention to disclose the reactivity matrix as defined above, wherein said antigens are attached to a substrate selected from a group consisting of microarray chip, microarray wafers, microarray strips, ELISA microwells, multiplex beads or any substrate known in the relevant art.

It is a further object of the present invention to disclose the reactivity matrix as defined above, wherein said antigens are selected form a group consisting of protein, polypeptide, peptide, nucleic acids, lipids, glycosylated molecules, polypeptides with modifications, polysaccharides or any other biological molecule known in the art.

It is a further object of the present invention to disclose the reactivity matrix as defined above, wherein said antibody reactivities are defined as IgG, IgM, IgA, IgE antibody isotypes or as more specific sub-isotypes of said antibodies.

It is a further object of the present invention to disclose the reactivity matrix as defined above, wherein said specific antibody reactivity is analyzable by using measuring means.

It is a further object of the present invention to disclose the reactivity matrix as defined above, wherein said specific antibody reactivity is analyzable by using labeling means.

It is a further object of the present invention to disclose the reactivity matrix as defined above, wherein said labeling means is adapted to label said human antibodies with a mixture of secondary antibodies specific for human immunoglobulin types to form a reactivity matrix.

It is a further object of the present invention to disclose the reactivity matrix as defined above, wherein said labeling means comprises labeling signal selected form a group consisting of fluorescent, chemiluminescent, absorptive, electronic, radioactive, paramagnetic or any labeling signal known in the art, or combination thereof.

It is a further object of the present invention to disclose the reactivity matrix as defined above, wherein said specific antibody reactivity is further analyzable by: (a) using a scanning means for scanning said reactivity matrix signal; (b) using a measuring means for measuring the intensity of said signal; (c) using generating and recording means for generating and recording results associated with said reactivity matrix signal; (d) using producing means for producing said results in the form of a signature, profile, set, pattern or matrix characteristic to said individual; and, (e) using means for comparing the results with a databank containing data concerning said antibody reactivities in populations susceptible to AMI, thereby identifying the development of an Acute Myocardial Infarction (AMI) process in said individual.

It is a further object of the present invention to disclose the reactivity matrix as defined above, wherein said measuring and scanning means are selected from a group consisting of Surface Plasmon Resonance (SPR), ellipsometry, laser scanning, light detecting, photon detecting via a photon multiplier, photographing with a digital camera based system or video system, radiation counting, fluorescence detecting, electronic, magnetic detecting or any other technique known in the art or combination thereof.

It is a further object of the present invention to disclose the reactivity matrix as defined above, wherein said reactivity is defined as a relative intensity of a specific antibody bound antigen as compared to its intensity signal in healthy control individuals.

It is a further object of the present invention to disclose the reactivity matrix as defined above, wherein said reactivity is defined as a relative intensity of a specific antibody bound antigen as compared to its intensity signal in individuals who have had a stroke event.

It is a further object of the present invention to disclose the reactivity matrix as defined above, wherein said reactivity is further defined as a set of informative antigens possessing a higher or a lower intensity reactivity signals as compared to said intensity signals of said antigens in said healthy control individuals.

It is a further object of the present invention to disclose the reactivity matrix as defined above, wherein said reactivity is further defined as a set of informative antigens possessing a higher or a lower intensity reactivity signals as compared to said intensity signals of said antigens in individuals who have had a stroke event.

It is another core object of the invention to disclose a system for recognizing the development of an Acute Myocardial Infarction (AMI) process in an individual. The aforementioned system comprising: (a) a substrate embedded with antigens; (b) biological fluid derived specimen containing a specific antibody repertoire; (c) means for physically contacting said specimen with the surface of said substrate; (d) means for binding said antibodies of said specimen to said antigens embedded in said substrate so as to form bound antibody antigen complexes; (e) a measuring device for quantifying the intensity signal of said bound antibodies; and, (f) a data processor for producing said intensity signals in the form of a signature, profile, set, pattern or matrix characteristic to said individual. According to certain embodiments of the present invention, some of the herein disclosed antigens are specific peptides. The aforementioned antigens are selected from a group consisting of Brain-1 oligo-dendrocyte transcription factor, Synaptotagmin 1, Tryptophan hydroxylase peptide 1, Tryptophan hydroxylase peptide 2, BSP (Brain specific protein), myelin associated glycoprotein, Fibronectin, Caspase 3, Myelin-associated metalloproteinase, CD68, Bone morphogenic protein 4 and D4GDI (GDP-dissociation inhibitor), further wherein said antigens are characterised by their specific reactivity with said specimen containing said antibodies associated with susceptibility to AMI, when bound under defined conditions.

It is a further object of the present invention to disclose the system as defined above, wherein said human antibodies are derived from a biological fluid specimen selected from a group consisting of plasma, serum, blood, cerebrospinal fluid, synovial fluid, sputum, saliva, tears, lymph specimen, or any biological fluid known in the art.

It is a further object of the present invention to disclose the system as defined above, wherein said antigens are attached to a substrate selected from a group consisting of microarray chip, microarray wafers, microarray strips, ELISA microwells, multiplex beads or any substrate known in the relevant art.

It is a further object of the present invention to disclose the system as defined above, wherein said antigens are selected form a group consisting of protein, polypeptide, peptide, nucleic acid, lipid, glycosylated molecules, polypeptides with modifications, polysaccharides or any other biological molecule known in the art.

It is a further object of the present invention to disclose the system as defined above, wherein said antibody reactivities are defined as IgG, IgM, IgA, IgE antibody isotypes or as more specific sub-isotypes of said antibodies.

It is a further object of the present invention to disclose the system as defined above, wherein said specific antibody reactivity is analyzable by using measuring means.

It is a further object of the present invention to disclose the system as defined above, wherein said specific antibody reactivity is analyzable by using labeling means.

It is a further object of the present invention to disclose the system as defined above, wherein said labeling means is adapted to label said human antibodies with a mixture of secondary antibodies specific for human immunoglobulin types to form a reactivity matrix.

It is a further object of the present invention to disclose the system as defined above, wherein said labeling means comprises labeling signal selected form a group consisting of fluorescent, chemiluminescent, absorptive, electronic, radioactive, paramagnetic or any labeling signal known in the art, or combination thereof.

It is a further object of the present invention to disclose the system as defined above, wherein said specific antibody reactivity is further analyzable by: (a) using a scanning means for scanning said reactivity matrix signal; (b) using a measuring means for measuring the intensity of said signal; (c) using generating and recording means for generating and recording results associated with said reactivity matrix signal; (d) using producing means for producing said results in the form of a signature, profile, set, pattern or matrix characteristic to said individual; and, (e) using means for comparing the results with a databank containing data concerning said antibody reactivities in populations susceptible to AMI, thereby identifying the development of an Acute Myocardial Infarction (AMI) process in said individual.

It is a further object of the present invention to disclose the system as defined above, wherein said measuring and scanning means are selected from a group consisting of Surface Plasmon Resonance (SPR), ellipsometry, laser scanning, light detecting, photon detecting via a photon multiplier, photographing with a digital camera based system or video system, radiation counting, fluorescence detecting, electronic, magnetic detecting or any other technique known in the art or combination thereof.

It is a further object of the present invention to disclose the system as defined above, wherein said reactivity is defined as a relative intensity signal of a specific antibody bound antigen as compared to its intensity signal in healthy control individuals.

It is a further object of the present invention to disclose the system as defined above, wherein said reactivity is defined as a relative intensity signal of a specific antibody bound antigen as compared to its intensity signal in individuals who have had a stroke event.

It is a further object of the present invention to disclose the system as defined above, wherein said reactivity is further defined as a set of informative antigens possessing a higher or a lower intensity reactivity signals as compared to said intensity signals of said antigens in said healthy control individuals.

It is a further object of the present invention to disclose the system as defined above, wherein said reactivity is further defined as a set of informative antigens possessing a higher or a lower intensity reactivity signals as compared to said intensity signals of said antigens in individuals who have had a stroke event.

It is another core object of the invention to disclose a kit useful for recognizing the development of an Acute Myocardial Infarction (AMI) process in an individual. The aforementioned kit comprising: (a) a set of antigens selected from a group consisting of Brain-1 oligo-dendrocyte transcription factor, Synaptotagmin 1, Tryptophan hydroxylase peptide 1, Tryptophan hydroxylase peptide 2, BSP (Brain specific protein), myelin associated glycoprotein, Fibronectin, Caspase 3, Myelin-associated metalloproteinase, CD68, Bone morphogenic protein 4 and D4GDI (GDP-dissociation inhibitor) attached to a substrate, wherein said antigens are further characterised by their specific ability to form bound antibody antigen reactivity complexes with human specimen containing antibodies associated with susceptibility to AMI; (b) a mixture of secondary labeled antibodies specific for human immunoglobulin types; (c) components or solutions useful for reacting said antigens with said antibodies of said specimen; (d) components or solutions useful for reacting said antigen antibody complexes with said secondary labeled antibodies; and, (e) instructions for reacting said antigens with said components and said complexes with said secondary antibodies in vitro so as to obtain results useful for identifying an Acute Myocardial Infarction (AMI) process in an individual.

It is a further object of the present invention to disclose the kit as defined above, wherein said antigens characterized by association with a variety of conditions selected from a group consisting of inflammation, angiogenesis, apoptosis or any other condition involving immune regulation or combination thereof.

It is a further object of the present invention to disclose the kit as defined above, wherein said human antibodies are derived from a biological fluid specimen selected from a group consisting of plasma, serum, blood, cerebrospinal fluid, synovial fluid, sputum, saliva, tears, lymph specimen, or any biological fluid known in the art.

It is a further object of the present invention to disclose the kit as defined above, wherein said antigens are attached to a substrate selected from a group consisting of microarray chip, microarray wafers, microarray strips, ELISA microwells, multiplex beads or any substrate known in the relevant art.

It is a further object of the present invention to disclose the kit as defined above, wherein said antigens are selected form a group consisting of protein, polypeptide, peptide, nucleic acid, lipid, glycosylated molecules, polypeptides with modifications, polysaccharides or any other biological molecule known in the art.

It is a further object of the present invention to disclose the kit as defined above, wherein said antibody reactivities are defined as IgG, IgM, IgA, IgE antibody isotypes or as more specific sub-isotypes of said antibodies.

It is a further object of the present invention to disclose the kit as defined above, wherein said specific antibody reactivity is analyzable by using measuring means.

It is a further object of the present invention to disclose the kit as defined above, wherein said specific antibody reactivity is analyzable by using labeling means.

It is a further object of the present invention to disclose the kit as defined above, wherein said labeling means are adapted to label said human antibodies with a mixture of secondary antibodies specific for human immunoglobulin types to form a reactivity matrix.

It is a further object of the present invention to disclose the kit as defined above, wherein said labeling means comprises labeling signal selected form a group consisting of fluorescent, chemiluminescent, absorptive, electronic, radioactive, paramagnetic or any labeling signal known in the art, or combination thereof.

It is a further object of the present invention to disclose the kit as defined above, wherein said specific antibody reactivity is further analyzable by: (a) using a scanning means for scanning said reactivity matrix signal; (b) using a measuring means for measuring the intensity of said signal; (c) using generating and recording means for generating and recording results associated with said reactivity matrix signal; (d) using producing means for producing said results in the form of a signature, profile, set, pattern or matrix characteristic to said individual; and, (e) using means for comparing the results with a databank containing data concerning said antibody reactivities in populations susceptible to AMI, thereby identifying the development of an Acute Myocardial Infarction (AMI) process in said individual.

It is a further object of the present invention to disclose the kit as defined above, wherein said measuring and scanning means are selected from a group consisting of Surface Plasmon Resonance (SPR), ellipsometry, laser scanning, light detecting, photon detecting via a photon multiplier, photographing with a digital camera based system or video system, radiation counting, fluorescence detecting, electronic, magnetic detecting or any other technique known in the art or combination thereof.

It is a further object of the present invention to disclose the kit as defined above, wherein said reactivity is defined as a relative intensity of a specific antibody bound antigen as compared to its intensity signal in healthy control individuals.

It is a further object of the present invention to disclose the kit as defined above, wherein said reactivity is defined as a relative intensity of a specific antibody bound antigen as compared to its intensity signal in individuals who have had a stroke event.

It is a further object of the present invention to disclose the kit as defined above, wherein said reactivity is further defined as a set of informative antigens possessing a higher or a lower intensity reactivity signals as compared to said intensity signals of said antigens in said healthy control individuals.

It is a further object of the present invention to disclose the kit as defined above, wherein said reactivity is further defined as a set of informative antigens possessing a higher or a lower intensity reactivity signals as compared to said intensity signals of said antigens in individuals who have had a stroke event.

It is another aspect of the invention to provide antigens such as synaptotagmin 1, tryptophan hydroxylase peptide 1, tryptophan hydroxylase peptide 2, BSP (Brain Specific Protein), as therapeutic agents or vaccines against the inflammatory process in AMI and stroke. Tryptophan hydroxylase is an exemplar of an informative antigen which may be useful for treating atherosclerosis. Mouse models are being employed for this purpose.

It is another core aspect of the invention to disclose a method for arresting the development of an AMI process in a patient. The aforementioned method comprising steps of: (a) profiling the specific antibody reactivities or biomarkers associated with AMI susceptibility, (b) determining the specific AMI associated antigens bound by said antibody repertoires of said individuals specimens; (c) designing a drug comprising at least one of said specific antigens or at least one epitope of said specific antigens; and, (d) administering said drug to said patient thereby arresting the development of an AMI process in a patient. The aforementioned profiling step comprises steps of: (i) attaching a set of defined antigens to a substrate; (ii) obtaining biological fluid derived specimens from a plurality of individuals in a population, each of said specimens containing their specific antibody repertoire; (iii) binding said antibody repertoire of each of said specimens to said attached antigens thereby forming bound antibody antigen complexes; and, (iv) analysing results obtained.

It is another core aspect of the invention to disclose a method for screening for candidate drugs for arresting the development of an AMI process, in a patient. The aforementioned method comprising the steps of: (a) profiling the specific antibody reactivities associated with AMI susceptibility of individuals, (b) determining the specific AMI associated antigens bound by said antibody repertoires of said individuals; and, (c) selecting said candidate drugs as appropriate for administration as immunotherapy for arresting the development of an AMI process, in an individual, wherein said candidate drug contains at least one of said specific AMI associated antigens or at least one epitope of said specific antigens. The aforementioned profiling step further comprising the steps of: (i) attaching a set of defined antigens to a substrate; (ii) obtaining biological fluid derived specimens from a plurality of individuals in a population, each of said specimens containing their specific antibody repertoire; (iii) binding said antibody repertoire of each of said specimens to said attached antigens thereby forming antibody antigen complexes; and, (iv) analysing results obtained.

BRIEF DESCRIPTION OF THE FIGURES

In order to understand the invention and to see how it may be implemented in practice, a plurality of embodiments is now described, by way of non-limiting example only, with reference to the accompanying drawings, wherein.

DETAILED DESCRIPTION OF THE INVENTION

Figure 1:
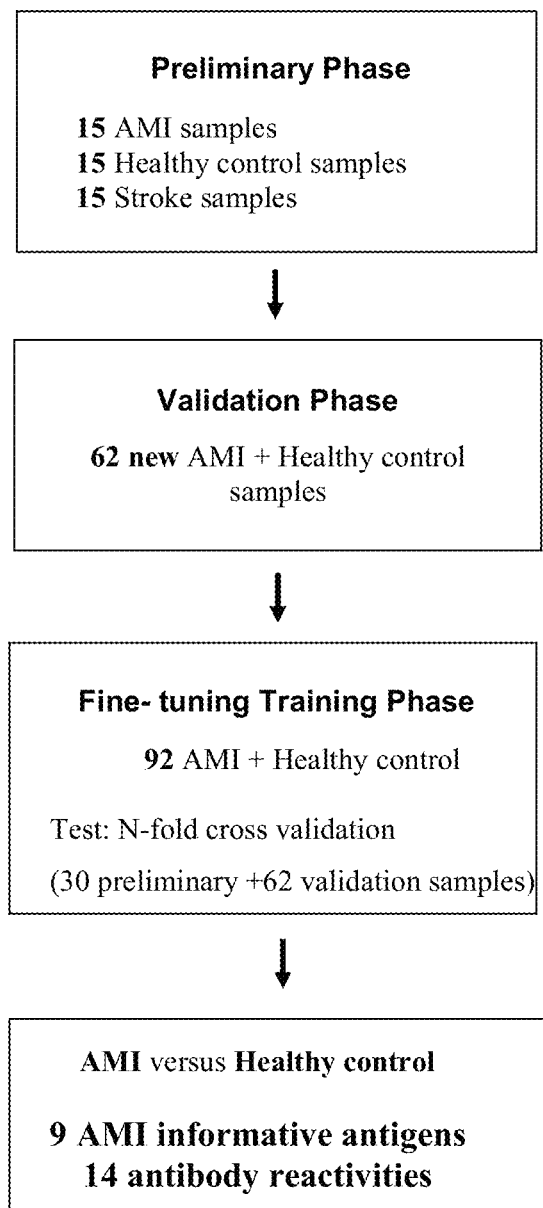
FIG. 1 is a flow diagram presenting the different phases leading to the elucidation of the AMI informative antigens of the present invention.

In the following description, various aspects of the invention will be described. For the purposes of explanation, specific configurations and details are set forth in order to provide a thorough understanding of the invention. However, it will be also apparent to one skilled in the art that the invention may be practiced without specific details presented herein. Furthermore, well-known features may be omitted or simplified in order not to obscure the invention.

It is herein disclosed that the present invention provides methods for identifying the development of an Acute Myocardial Infarction (AMI) process in an individual. More specifically, the current invention discloses a set of informative antibody reactivities which surprisingly and unexpectedly, are capable of identifying the development of an AMI process in an individual.

It is within the scope of the invention to disclose a set of informative antigens which unpredictably can discriminate between an AMI process and an impending stroke event in an individual.

As is known, Acute Myocardial Infarction (AMI), also known as a heart attack, occurs when the blood supply to part of the heart is interrupted. This is most commonly due to occlusion (blockage) of a coronary artery following the rupture of a vulnerable atherosclerotic plaque. The aforementioned plaque consists of an unstable collection of lipids (like cholesterol) and white blood cells (especially macrophages) in the wall of an artery. The resulting ischemia (restriction in blood supply) and oxygen shortage, if left untreated for a sufficient period, can cause damage and/or death (infarction) of heart muscle tissue (myocardium).

A stroke is the rapidly developing loss of brain functions due to a disturbance in the blood vessels supplying blood to the brain. This can be due to ischemia (lack of blood supply) caused by thrombosis or embolism or due to a hemorrhage. As a result, the affected area of the brain is unable to function, leading to inability to move one or more limbs on one side of the body, inability to understand or formulate speech or inability to see one side of the visual field. Stroke is also referred to as Cerebrovascular Event or CVE.

Thus, both AMI and stroke conditions are acute vascular events which result from atherosclerotic processes but in different locations in the vascular system.

Hence, the herein disclosed ability to discriminate between Acute Myocardial Infarction (AMI) and stroke is significant and unexpected. It is highly novel that the present invention can discriminate between different variations of atherosclerosis process.

As used herein the terms 'autoimmunity', or 'autoreactivity' or 'autoantibodies' refer to the immune system which expresses both the genetic endowment of the individual and the life experience of the individual. The immune system in both its innate and adaptive arms can be viewed as a type of biological health-maintenance system. Health maintenance, performed by the immune system, requires access of the system to information regarding the biologic state of the body. Towards this aim, the immune system, like health-maintenance systems generally, needs biomarkers.

The immune system must be sensitive to the state of the body and intimately responsive to it, thus autoimmunity has to be built into the system and a degree of autoimmunity must be physiological.

As suggested by Prof Cohen and Prof. Sahar's research groups, many natural antibodies detected in healthy subjects are autoantibodies; which bind self-molecules [3, 22]. The specific self-molecules recognized by these autoantibodies appear to form clinically defining signatures: some autoantibodies create a pattern that heralds susceptibility to a future disease, e.g. an autoimmune disease [3, 22], while a different autoantibody pattern can mark resistance to the disease.

It has been proposed that the natural autoantibodies and auto-reactive T cells in healthy individuals may be directed to a specific and limited set of self-molecules; this selective autoimmunity has been termed the immunological homunculus or immunculus—the immune system's internal representation of the body. An important function of the immunological homunculus is to create and detect biomarkers.

The autoantibodies which are presented at birth in the human cord blood—the congenital immunological homunculus—were studied using an antigen microarray chip [2]. IgG, IgA and IgM antibody types, binding to about 300 self-antigens, were surveyed. These autoantibody reactivities that were found by the abovementioned research groups provides the immune system with the right kind of biomarker information about body state, needed to manage a healthy inflammatory program.

Thus, it was proposed by the researches that the immunological homunculus helps in maintaining health in the following ways:

Natural autoimmunity could help the body remove troublesome waste molecules and cells [23].

Natural autoimmune T cells and B cells and autoantibodies could provide an early immune response to pathogens expressing molecules that are cross-reactive with particular self-antigens.

Natural autoimmunity is also proposed to prevent pathogenic autoimmunity by generating regulatory circuits or by blocking the access of potentially pathogenic agents to key self-antigens [3].

It is within the scope of the present invention to disclose the self-antigens recognized by homuncular agents identified as biomarkers that inform the immune system of the state of the body, both locally and globally. This enables to gain insight into health and disease conditions of the body, by studying an individual's patterns of autoimmunity.

It is herein disclosed that the immunological homunculus, as a natural biomarker system for immune health-maintenance, might serve as a medical health-maintenance system. Moreover, in accordance with a further aspect of the present invention, identifying the biomarker system of an individual might be useful in adjusting correct medicine for a patient.

As used herein, the term 'Cardiovascular disease' refers to any disease that involves the heart or blood vessels (arteries and veins), and more specifically it refers to atherosclerosis, which is an arterial disease. Types of cardiovascular diseases include: Aneurysm, Angina, Atherosclerosis, Cerebrovascular Accident (Stroke), Cerebrovascular disease, Congestive Heart Failure, Coronary Artery Disease and Myocardial infarction (Heart Attack). These conditions have similar causes, mechanisms, and treatments.

It is herein acknowledged that the present invention discloses methods and means of recognizing the development of a cardiovascular disease (CVD) in an individual. The aforementioned CVD's arise from all types of cardiovascular diseases listed below in a non limiting manner:

Aneurysm Angina Arrhythmia Atherosclerosis, Cardiomyopathy, Cerebrovascular Accident (Stroke), Cerebrovascular disease, Congenital heart disease, Congestive Heart Failure, Myocarditis, Valve Disease, Coronary Artery Disease, Dilated cardiomyopathy, Diastolic dysfunction, Endocarditis, High Blood Pressure (Hypertension), Hypertrophic cardiomyopathy, Mitral valve prolapsed, Myocardial infarction (Heart Attack), Venous Thromboembolism Ischaemic.

Acute coronary CHD: CAD—Coronary thrombosis—Coronary vasospasm—Coronary artery aneurysm Angina pectoris (Prinzmetal's angina)—Myocardial infarction (heart attack) Myocardial rupture—Dressler's syndrome Layers Pericarditis Pericarditis (Acute, Constrictive)—Pericardial effusion—Cardiac tamponade—Hemopericardium Myocardium Myocarditis Cardiomyopathy: Dilated (Alcoholic)—Hypertrophic—Restrictive (Loeffler endocarditis, Cardiac amyloidosis) Arrhythmogenic right ventricular dysplasia Endocardium/valves Endocarditis (Subacute bacterial endocarditis, Libman-Sacks endocarditis, Nonbacterial thrombotic endocarditis) mitral (regurgitation, prolapse, stenosis)—aortic (stenosis, insufficiency)—tricuspid (stenosis, insufficiency)—pulmonary (stenosis, insufficiency) Conduction/arrhythmia. Heart block AV (1°, 2°, 3°)—Bundle branch (Left, Right)—Bifascicular/Trifascicular—Sinoatrial—Sick sinus syndrome—Adams-Stokes syndrome Pre-excitation syndrome Wolff-Parkinson-White—Lown-Ganong-Levine.

Tachycardia Paroxysmal—Supraventricular (AV nodal reentrant, Accelerated idioventricular rhythm, Sinus)—Ventricular (Torsades de pointes, Catecholaminergic polymorphic) Premature contraction Atrial—Ventricular Flutter/fibrillation Atrial flutter—Ventricular flutter—Atrial fibrillation (Familial)—Ventricular fibrillation.

Pacemaker Wandering pacemaker—Ectopic pacemaker—Parasystole Long QT syndrome Romano-Ward syndrome—Andersen-Tawil syndrome—Jervell and Lange-Nielsen syndrome Cardiac arrest Sudden cardiac death—Asystole Other Cardiomegaly—Ventricular hypertrophy (Left, Right/Cor pulmonale) Heart failure (Cardiac asthma)—Rheumatic fever Arterial occlusive disease/peripheral vascular disease Arteriosclerosis: Atherosclerosis—Intermittent claudication—Atheroma—Monckeberg's arteriosclerosis Stenosis (Renal artery stenosis, Carotid artery stenosis)—Fibromuscular dysplasia—Degos disease—Aortoiliac occlusive disease Raynaud's phenomenon/Raynaud's disease—Erythromelalgia Aneurysm Aortic aneurysm/Abdominal aortic aneurysm—Cerebral aneurysm—Coronary artery aneurysm—Intracranial berry aneurysm—Dissection (Aortic, Carotid, Vertebral)—Pseudoaneurysm Other Arteritis (Aortitis)—Buerger's disease Arteriovenous fistula—Hereditary hemorrhagic telangiectasia Nevus (Spider angioma, Halo nevus) Venous thrombosis/Phlebitis/Thrombophlebitis primarily lower limb (Deep vein thrombosis) abdomen (May-Thurner syndrome, Portal vein thrombosis, Budd-Chiari syndrome, Renal vein thrombosis) upper limb (Paget-Schroetter disease) head (Cerebral venous sinus thrombosis) Post-thrombotic syndrome Varicose veins Varicocele—Gastric varices—Portacaval anastomosis (Hemorrhoid, Esophageal varices, Caput medusae) Other Superior vena cava syndrome—Inferior vena cava syndrome—Venous ulcer Arteries or veins Vasculitis—Thrombosis—Embolism (Pulmonary embolism, Cholesterol embolism)—Angiopathy (Macroangiopathy, Microangiopathy) Lymphatic disease Lymphadenitis—Lymphedema—Lymphangitis Blood pressure Hypertension Hypertensive heart disease—Hypertensive nephropathy—Secondary hypertension (Renovascular hypertension)—Pulmonary hypertension Hypotension Orthostatic hypotension Certain conditions originating in the perinatal period Maternal factors and complications Umbilical cord prolapse—Nuchal cord—Chorioamnionitis Cardiovascular Pneumopericardium—Persistent fetal circulation Haemorrhagic and haematological/hematologic disease Haemorrhagic disease of the newborn—Hemolytic disease of the newborn—Rh disease—Hydrops fetalis—Hyperbilirubinemia (Kernicterus, Neonatal jaundice) and other disorders Periventricular leukomalacia—Gray baby syndrome—muscle tone (Congenital hypertonia, Congenital hypotonia)—Perinatal infection (Congenital rubella syndrome)—Velamentous cord insertion—Omphalitis.

As used herein, the term 'antibody reactivity' or 'autoantibody reactivity' refers to the specific antigen-antibody binding which is elicited by the presence of a given antigen. The antibody or collective of different antibodies can recognize and bind to the antigen, specific epitopes on an antigen and/or different conformations of the antigen. Individual sera can be defined by multiplicities of different antibodies binding to different antigens, each antigen being recognized by a different antibody or different set of antibodies. The antibody reactivities which are formed with a specific defined set of antigens, associated with susceptibility to Acute Myocardial Infarction (AMI) or Stroke, are predictive of AMI or Stroke in an individual.

The term 'antibody repertoire' used herein refers to the present repertoire of antibodies in an individual's sample. This collection of antibodies encodes the history of the individual's past immunological experience, as well as the present state of the individual's body. It is within the scope of the invention to disclose means and methods of predicting resistance or susceptibility of an individual to the future development of an AMI and/or stroke condition by profiling the present autoantibody repertoire of an individual.

The term 'substrate' used herein refers in a no limiting manner to a microarray chip, microarray wafers, microarray strips, ELISA microwells, multiplex beads or any other substrate material known in the relevant art.

The term 'biological fluids' used herein refers in a non limiting manner to plasma, serum, blood, cerebrospinal fluid, synovial fluid, sputum, saliva, tears, lymph specimen of an individual or any other biological fluid known in the art.

The term 'defined antigens' used herein refers to at least 740 body molecules associated with a variety of conditions selected from a group consisting of inflammation, angiogenesis, apoptosis or any other condition involving immune regulation or combination thereof. The term 'informative antigens' used herein refers to antigens whose participation in antibody binding can discriminate between AMI, Stroke and Healthy control serum samples groups.

The term 'intensity' used herein refers to the signal strength generated by scanning, measuring or observing antibody-antigen binding. For example, a collection of antibody reactivities, expressed as signal intensities, makes up a profile for any given individual. Elevated levels of antibody production relative to the Healthy controls are picked up as elevated intensities on a results matrix.

The term 'susceptibility' used herein refers to the likelihood or probability of a patient to suffer an AMI and/or Stroke.

The term 'epitope' used herein refers to antigenic determinant, which is the part of a molecule that is recognized by the immune system, specifically by antibodies, B cells, or T cells.

The term 'human immunoglobulin types' used herein refers to different isotypes of the human antibodies.

The term 'sensitivity' of a diagnostic test used herein refers to the probability that an individual with a specific medical condition will be defined as such by the diagnostic test; i.e. the number of true positive test results divided by the number of all individuals tested who have the condition. The term also refers to the studies undertaken to establish useful informative antigens and antibody reactivities referred to herein.

The term 'specificity' of a diagnostic test used herein refers to the probability that an individual not having a specific medical condition will be correctly defined by the test; i.e. the number of true negative test results divided by the number of control specimens tested. The term also refers to the studies undertaken to establish useful informative antigens and antibody reactivities referred to herein.

The term 'accuracy' of a diagnostic test used herein refers to the fraction of correct results provided by the test. The term also refers to the studies undertaken to establish useful informative antigens and antibody reactivities referred to herein.

The term 'PPV' used herein refers to the probability that an individual with a positive test result indeed has the medical condition indicated by the test.

The term 'NPV' used herein refers to the probability that an individual with a negative test result is indeed free of the medical condition indicated by the test.

Thus the present invention provides a method of recognizing the development of an Acute Myocardial Infarction (AMI) process in an individual. The aforementioned method comprises steps of: profiling specific antibody reactivities or biomarkers associated with AMI susceptibility and analysing results obtained. The aforementioned profiling step further comprises steps of: (a) attaching a set of defined antigens to a substrate; (b) obtaining a biological fluid derived specimen from an individual, said specimen containing a specific antibody repertoire; and, (c) binding said antibodies of said biological fluid specimen to said attached antigens thereby forming bound antibody antigen complexes.

Moreover, the present invention provides means and methods to differentiate diagnoses of stroke and AMI. The finding that stroke and AMI differ in their antigen chip signature is highly novel, even though both conditions have been assumed to involve similar atherosclerotic processes. The diagnostic methods for stroke provided herein are particularly useful in differentiating from brain tumors for example, which may present with similar initial symptoms.

It is within the scope of the invention that the defined antigens which are attached to the substrate, as detailed above, are characterized by their association with a variety of conditions selected from a group consisting of inflammation, angiogenesis, apoptosis or any other condition involving immune regulation or combination thereof.

It is further within the scope of the invention to provide antigens such as synaptotagmin 1, tryptophan hydroxylase peptide 1, tryptophan hydroxylase peptide 2, BSP (Brain Specific Protein), for their as therapeutic agents or vaccines against the inflammatory process in AMI and stroke. Tryptophan hydroxylase is an exemplar of an informative antigen which may be useful for treating atherosclerosis. Mouse models are being employed for this purpose. The references of Appendix I are included in their entirety.

EXAMPLES

In order to understand the invention and to see how it may be implemented in practice, a plurality of preferred embodiments will now be described by way of non-limiting example only, with reference to the following examples.

Example 1

Identifying Autoantibody Reactivities Discriminating Between AMI and Healthy Control Serum Samples Reference is now made to FIG. 1 illustrating a flow diagram describing the different phases of the study detailed below. The study aimed to elucidate informative antigens which are associated with the development of an AMI process in an individual. As detailed in FIG. 1, the study includes the following phases:

1. Preliminary Phase
I. Aim

The rationale behind the study summarized herein is to provide a classifier or an algorithm which can discriminate between healthy individuals and individuals who are at high risk for the development of an AMI process. Moreover, the study is aimed to discover biomarkers which distinguish between individuals having an AMI process and individuals with a stroke event. The aforementioned study tests the capability of the antigen microarray chip to discriminate in a blinded test between three groups of serum samples: Acute Myocardial Infarction (AMI) and stroke samples, and a group of healthy control samples. The results serve as a disclosure of the present invention and as basis for further variations and improvements of the invented method.

II. Materials and Methods

Specimens: Three groups of serum samples, each group containing 15 samples. Patient specimens were collected between 1 and 4 months after an acute event.

a. 15 patients with a recent Acute Myocardial Infarction (AMI)—group 4.
b. 15 patients with a recent Stroke—group 2.
c. 15 Healthy controls—group 0.

The aforementioned specimens were coded (labeled "0", "2", "4"), so that the tester was blinded to the identity of each specimen group during the testing and analysis of the results.

An Antigen microarray Chip (I-Chip) was used, bearing over 740 body molecules (herein antigens) related to a variety of conditions—immune regulation, inflammation, angiogenesis, apoptosis and more.

Reference is now made to Quintana et al., 2004 [1] describing the preparation of antigen microarray chips and the process of image and data analysis used for the identification of predictive antibody repertoire associated with induced diabetes in mice.

It is herein disclosed that the antigen microarray chips were produced, and the specimens were tested, as described by Quintana et al., 2004 [1].

Data Analysis:

The output of the experiment was a set of 45 (3 groups of 15 specimens in each group) scanned slide images. The images obtained by laser scanning of each microarray slide, were automatically preprocessed to quantify the antibody-binding signal for each antigen spot on the array and produce a reactivity matrix. The (i,j)'th entry in this matrix corresponds to the reactivity of the i'th antibody in the j'th specimen.

This matrix was used to build a classifier that was able to predict the class identity of unseen specimens. To validate the performance of the classifier, we applied N-fold cross-validation, i.e. a Leave-One-Out (LOO) procedure. In this procedure, a single specimen is set aside, while the rest of the specimens are used to build a classifier, which is then tested on the left-out specimen. This process is repeated over all specimens, and the total number of errors—the LOO error—estimates the performance of the classifier.

A separate classifier was built in each LOO instance. More specifically, feature selection was first performed over the left-in specimens; this entailed choosing which of the antigens may be suitable for discriminating between the classes, and then build a classifier based on these antigens. In the present case, feature selection was done by ranking the different antigens according to a mutual information criterion. Classification was based on the selected antigens, using a nearest-neighbor classifier, or a linear support vector machine.

To estimate the statistical significance of the findings, a permutation test was performed. The different specimens were repeatedly assigned random labels, and the LOO procedure was then performed. For each set of random labels, we estimated the LOO error, and compared it to the LOO error based on the correct labels. An estimated p-Value is then computed based on the number of such random permutations whose LOO error is lower than or equal to the case of correct labels.

III. Results

The individual samples in each of the groups were compared in a pair-wise manner:

a. The AMI group ("4") versus the Healthy control group ("0").

b. The Stroke group ("2") versus the Healthy control group ("0").

c. The Stroke group ("2") versus the AMI Group ("4").

AMI Group ("4") Versus the Healthy Control Group ("0")—

Reference is now made to Table 1 presenting the analysis of the antigen microarray chip.

TABLE 1

| AMI ("4") versus Healthy control ("0") | | | | |
|---|---|---|---|---|
| | | CLINICAL DEFINITION | | |
| I-CHIP | | 4 | 0 | |
| | 4 | 14 | 2 | 16 |
| | 0 | 1 | 13 | 14 |
| | | 15 | 15 | 30 |
| SENSITIVITY | | | 93.3 | |
| SPECIFICITY | | | 86.7 | |
| PPV | | | 87.5 | |
| NPV | | | 92.9 | |

The numbers provided in the table indicate the total number of times the antigen microarray chip provided a "4" or a "0" result. This is used in the calculation of the predictive values (positive & negative).

Analysis of the results comparing between the stroke group and the healthy control group as well as between the stroke group and the AMI group is presented below in Example 2.

Figure 2:
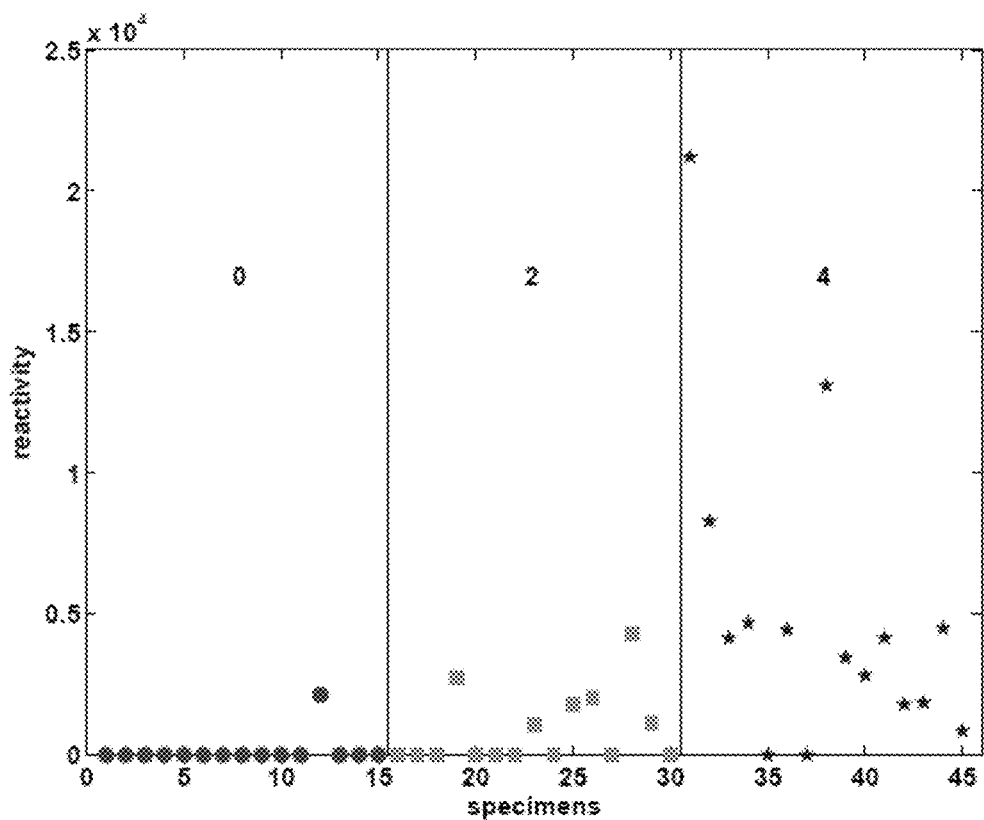
FIG. 2 is a graphic illustration representing the antibody reactivity levels of Tryptophan hydroxylase (peptide 1) informative antigen in each of the three specimen groups.

The Most Informative Antigen:

Interestingly, the results obtained revealed that a peptide of Tryptophan hydroxylase (TPH) (peptide 2) was by itself able to separate to a large extent between the three groups. FIG. 2 shows the antibody reactivity levels of Tryptophan hydroxylase antigen in the three specimen groups "0", "2" and "4".

As illustrated, the reactivity level against Tryptophan hydroxylase (TPH) antigen is most significant in the AMI group ("4"), intermediate in the Stroke group ("2") and almost non detectable in the Healthy control group ("0"). Thus, according to the described results, the antibody reactivity level for Tryptophan hydroxylase antigen can effectively discriminate between AMI Healthy control specimens, with only 3 errors in the LOO test; and could separate the Stroke group from the Healthy control group with only six errors.

IV. Conclusions:

An unsupervised analysis using the 740 microarray chip antigens detects a highly correlated subgroup of informative antigens formed by samples appearing in each of the 3 groups.

Both the AMI ("4") and the Stroke ("2") groups can be discriminated from the Healthy control group ("0") with sensitivities and specificities of about 90%.

The most informative antigen was a peptide of Tryptophan hydroxylase, to which the AMI patients manifested an elevated level of antibody production relative to the healthy controls.

2. Validation Phase

The aim of the study described herein was to validate the results obtained in the preliminary phase, by testing additional new 62 serum samples representing AMI and Healthy control groups, using the same classifier as described in the preliminary phase.

Analysis of the autoantibody reactivity patterns confirms the novel finding that Tryptophan hydroxylase peptide 1 can function as an informative antigen or biomarker for atherosclerotic conditions and can be used to discriminate AMI patients from healthy controls (FIG. 3A), as was found in the preliminary phase.

Figure 3A:
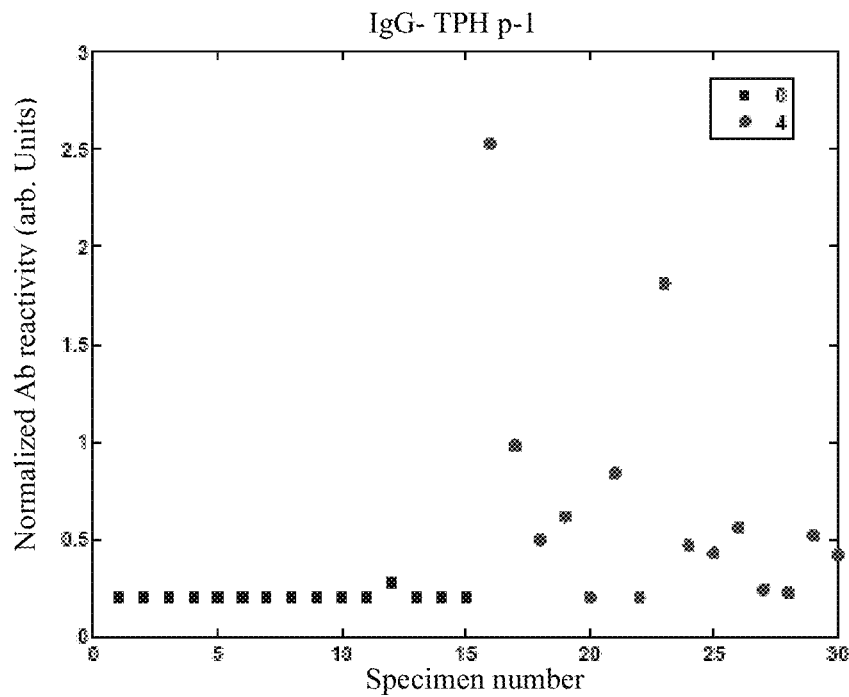
FIG. 3A is a graphic illustration representing the antibody reactivity levels of Tryptophan hydroxylase (peptide 1) antigen in Acute Myocardial Infarction (AMI) versus the Healthy control specimen groups.
Figure 3B:
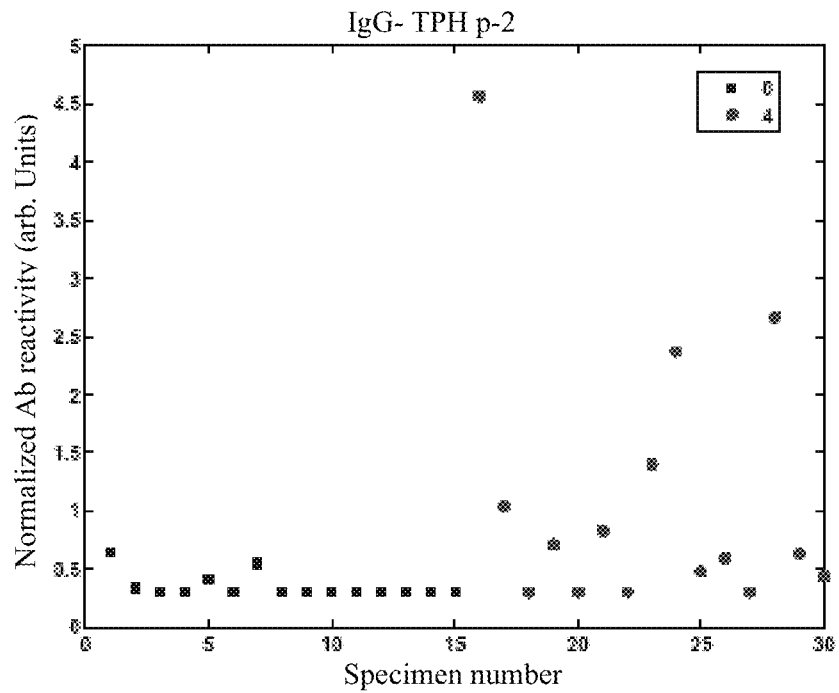
FIG. 3B is a graphic illustration representing the antibody reactivity levels of Tryptophan hydroxylase (peptide 1) antigen in Acute Myocardial Infarction (AMI) versus the Healthy control specimen groups.

Three additional antigens were also informative, all with higher antibody reactivities in the AMI patients:

a second peptide of Tryptophan hydroxylase (peptide 2), as presented in FIG. 3B;

a peptide of synaptotagmin1, as presented in (FIG. 3D); and, a peptide of Brain-1, an oligodendrocyte transcription factor.

A classifier based on these four antigens provided the following performance in a LOO test:
SENSITIVITY 93%
SPECIFICITY 87%
PPV 88%
NPV 91%

Thus, two different peptides of Tryptophan hydroxylase (peptides 1 and 2) separated the AMI group from the healthy control group with a high degree of accuracy as indicated in FIGS. 3A and 3B.

Figure 3C:
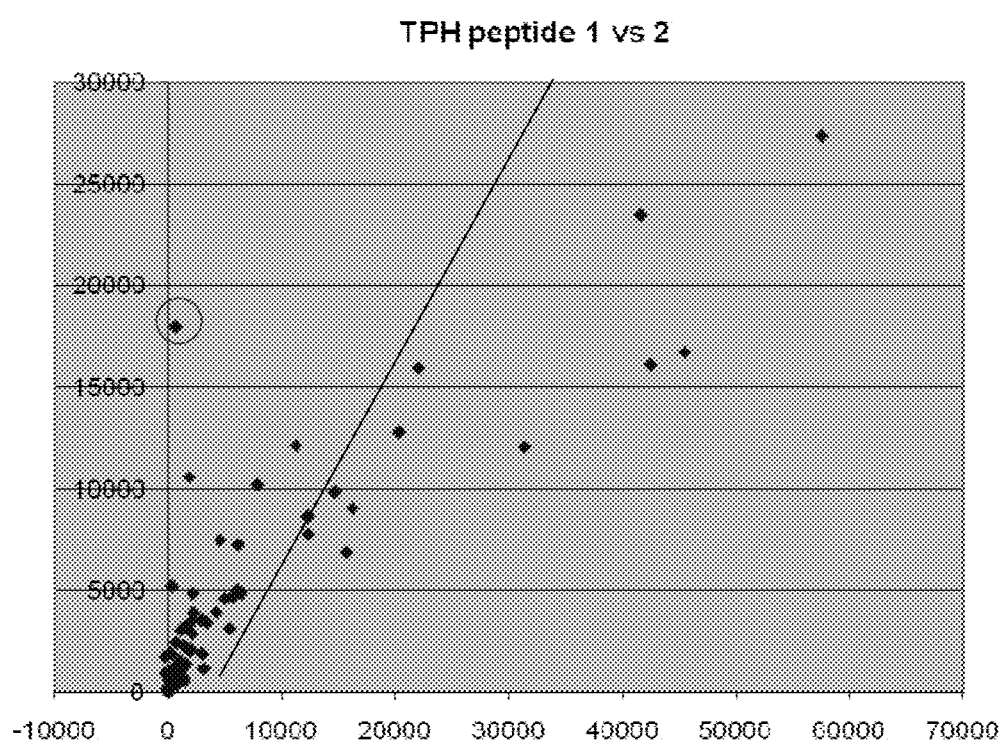
FIG. 3C is a graphic illustration representing the correlated antibody reactivity levels of Tryptophan hydroxylase peptides 1 and peptide 2 in Acute Myocardial Infarction (AMI) versus the Healthy control specimen groups.
Figure 3D:
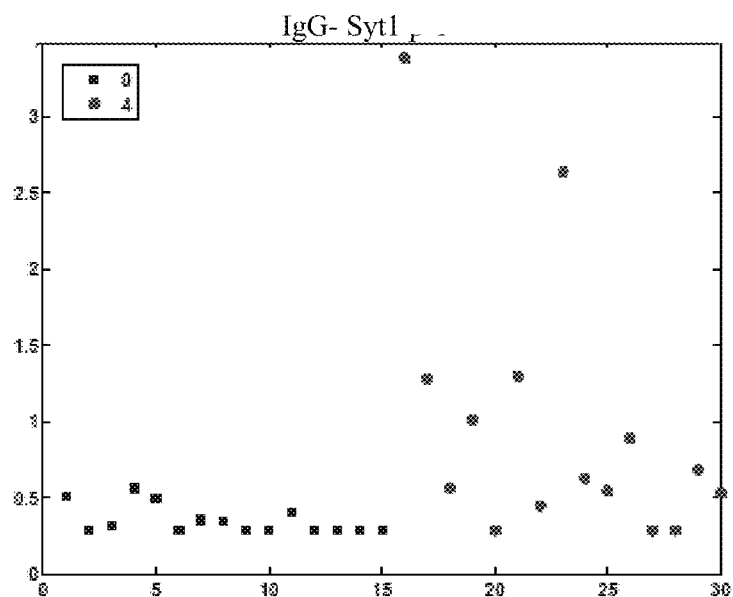
FIG. 3D is a graphic illustration representing the antibody reactivity levels of synaptotagmin1 antigen in Acute Myocardial Infarction (AMI) versus the Healthy control specimen groups.
Figure 4A:
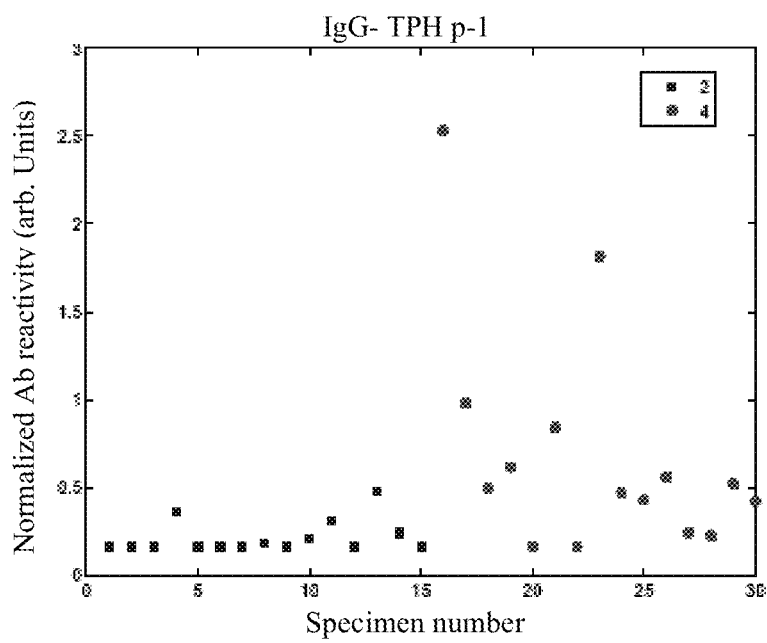
FIG. 4A is a graphic illustration representing the antibody reactivity distribution of Tryptophan hydroxylase (peptide 2) antigen in the AMI versus the Stroke specimen groups.
Figure 4B:
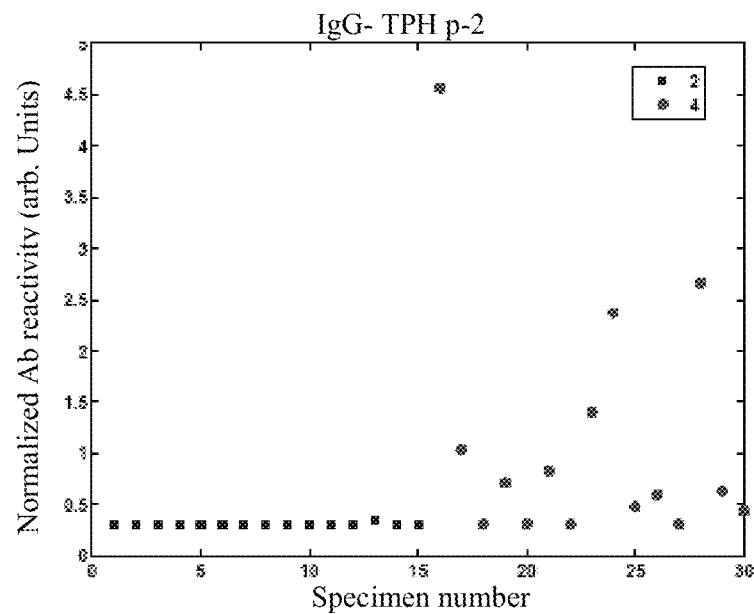
FIG. 4B is a graphic illustration representing the antibody reactivity distribution of Tryptophan hydroxylase (peptide 1) antigen in the AMI versus the Stroke specimen groups.
Figure 4C:
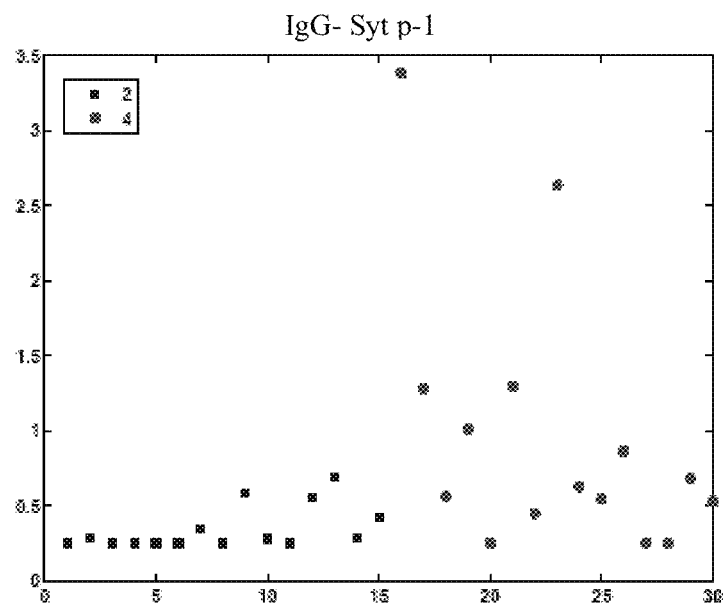
FIG. 4C is a graphic illustration representing the antibody reactivity distribution of Synaptotagmin1 antigen in the AMI versus the Stroke specimen groups.
Figure 4D:
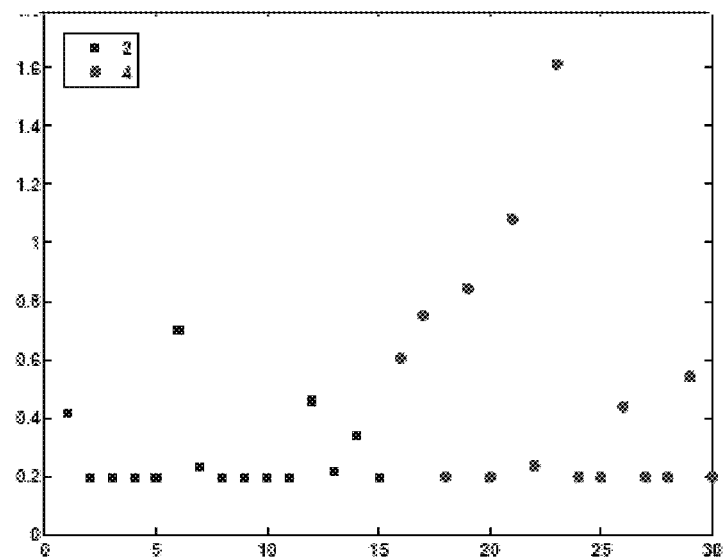
FIG. 4D is a graphic illustration representing the antibody reactivity distribution of Myelin-Associated Metalloproteinase antigen in the AMI versus the Stroke specimen groups.
Figure 4E:
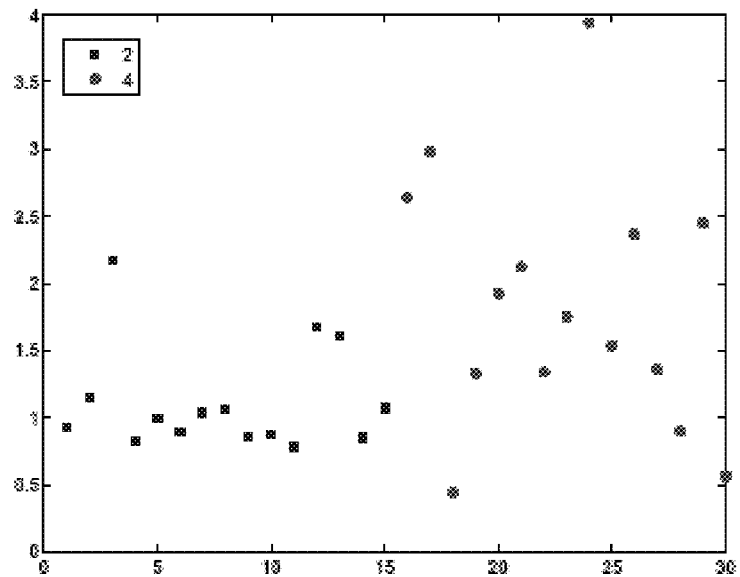
FIG. 4E is a graphic illustration representing the antibody reactivity distribution of Bone Morphogenic Protein 4 (BMP4) antigen in the AMI versus the Stroke specimen groups; and, FIG. 4F is a graphic illustration representing the antibody reactivity distribution of GDP-Dissociation Inhibitor (D4GDI) antigen in the AMI versus the Stroke specimen groups.
Figure 4F:
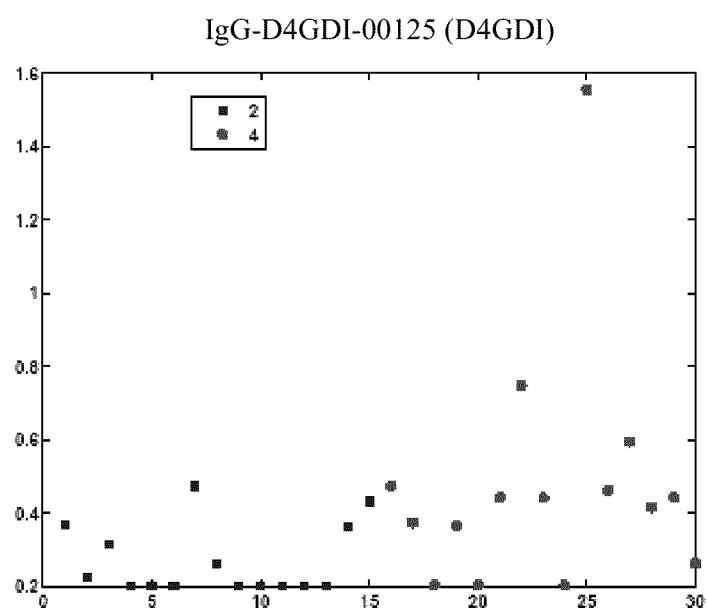

Reference is now made to FIG. 3C showing a comparison of the reactivity levels of TPH peptides 1 and 2. As shown, most AMI subjects respond strongly to one or both of the abovementioned antigens and few AMI subjects have only low responses, in the range of the healthy control subjects. These low-reactor AMI subjects might have confounding factors that set them apart. For example, the specimen marked with a red circle would be considered negative according to peptide 1 (thus yielding a false negative result), but reacts positively with peptide 2. Thus, some of the low responders to one of the peptides have higher responses to the other peptide. Therefore both peptides together have fewer false negatives.

Other antigens showing increased reactivity in the AMI group as compared to the healthy control group are peptides of synaptotagmin1 (see FIG. 3D), and a peptide of Brain-1, an oligodendrocyte transcription factor. The association of both antigens to cardiovascular diseases is novel.

Thus, the correlation between the presence of autoantibodies against particular molecules and the nature of the expression of these molecules and their function is an important outcome of these experiments.

The finding of markedly increased reactivity against few antigens such as Tryptophan hydroxylase suggests that it is possible to construct a method of classification based on these reactivities and not based on clustering. The importance of Tryptophan hydroxylase in blood vessel pathophysiology and cardiovascular disease is well known. The novelty of the present invention is that the immune system uses Tryptophan hydroxylase as an immune biomarker.

3. Training Phase

I. Introduction

The aim of this study was to refine the classification algorithms based on autoantibody reactivity patterns of AMI and healthy control groups by using ImmunArray's antigen chip microarray. Towards this aim the 62 specimens analysed in the validation phase were combined with the 30 specimens of the preliminary phase to generate a new training set of AMI and Healthy control specimens. All 92 specimens were re-analyzed as one, expanded training group in order to identify additional informative antibody reactivities and obtain a refined classification rule.

II. Results

The combined set of 92 specimens was analyzed (50 AMI and 42 Healthy controls) to search for additional antigens and to refine the classification algorithm. Five antigens, in addition to the 4 defined above under "validation phase", were found to discriminate between the AMI patients and the Healthy controls with statistical significance (FDR>0.05). Some of the antigens elicited both IgG and IgM production, providing in total 14 informative antibody reactivities, which define 9 different informative antigens, as listed in the following Table 2.

TABLE 2

Informative antibody reactivities of AMI versus Healthy control groups.

| Name | Antigen type | GI Accession# or reference | Immuno-globulin type | Antibody level in AMI | peptide Sequence |
|---|---|---|---|---|---|
| Brain-1, oligo-dendrocyte transcription factor | peptide | 2760445 | IgG, IgM | up | DPSSVKMVQSDFMQGAMAA |
| Synaptotagmin 1 | peptide | 1351176 | IgG, IgM | up | NESFSFEVPFEQIQKVQVVV |
| Tryptophan hydroxylase peptide 1 | peptide | 136122 | IgG, IgM | up | PLLKSHTTVLSVDSPDQLP |
| Tryptophan hydroxylase peptide 2 | peptide | 136122 | IgG, IgM | up | KSITSAMNELRHDLDVVND |
| BSP (Brain specific protein, myelin associated glycoprotein) | peptide | 206781 | IgG, IgM | up | TVSILCSTQSNPDPILTIF |
| Fibronectin | whole molecule | Sigma-Aldrich cat # F0895 | IgG | up | NA |
| Caspase 3 | peptide | Sigma-Aldrich cat # C1224 | IgM | down | MACHKIPVEADFLYAYSTAP |

TABLE 2-continued

Informative antibody reactivities of AMI versus Healthy control groups.

| Name | Antigen type | GI Accession# or reference | Immuno-globulin type | Antibody level in AMI | peptide Sequence |
|---|---|---|---|---|---|
| Myelin-associated metallo-proteinase | whole molecule | Sigma-Aldrich cat # A9975 | IgM | up | NA |
| CD68 | whole molecule | Prospec cat # PRO-293 | IgM | up | NA |

The specimens were classified with the following performance:
Sensitivity 87%
Specificity 82%
Accuracy 84%

IV. Summary & Discussion

Implementation of the above described preliminary phase, the validation phase and the training phase enabled the discovery of the novel 14 antibody reactivities, which recognize 9 informative antigens. These reactivities characterize a recent Acute Myocardial Infarction (AMI) in a patient and thus can recognize the development of an AMI process in an individual. The following conclusions may be drawn:

1. The autoantibody reactivities that were found to discriminate AMI patients from healthy control group were validated in a blind test performed on an independent group of test set specimens.
2. The amplified training set made it possible to identify additional antigen reactivities and resulted in an improved classifier, with both sensitivity and specificity of over 80%.
3. The informative antigen reactivities have not been previously reported to be immunologically involved in the disease pathogenesis, although some of the antigens are known to function in vascular physiology. Thus the discovery of their ability to be informative for vascular conditions is most significant. Moreover, there appears to be biological reasons for the targeting of these molecules by the immune system as immune biomarkers.

Example 2

Identifying Informative Autoantibody Reactivities Associated with Stroke

The antibody reactivity profiles of the 15 Stroke specimens of the above described preliminary phase of Example 1 were compared to the Healthy control antibody reactivity profiles as well as to the AMI specimen groups by analyzing the antigen microarray chip results. The data analysis was performed as described in Example 1.

a. The Stroke Group ("2") Versus the Healthy Control Group ("0")

A set of antigens that separated the stroke group from the healthy control group with 5 errors (83% accuracy) in a LOO test, is listed in Table 3.

TABLE 3

Stroke group versus Healthy control group

| Antigen name | Antigen full name | Antigen type | sequence | Immuno-globulin type | up/down regulated |
|---|---|---|---|---|---|
| NOGO | Nogo-66 (1-40) antagonist peptide (Sigma cat # N7161) | peptide | | IgM | down |
| P53 | p53 | peptide | CTYSPPLNKLFCQLVKTCPV | IgM | down |
| MAZ | MYC-associated zinc finger protein (purine binding transcription factor) | peptide | RHEAIHTHLNSHVRQVHS | IgG | down |
| GAD | Glutamic acid decarboxylase | peptide | GTDSVILIKQKGFVPFLVSA | IgM | down |
| C P450 | Cytochrome C P450 | whole molecule | NA | IgG | down |
| P53 | p53 mutant | whole molecule | NA | IgM | down |
| Tropomyosin | Tropomyosin | whole molecule | NA | IgG | down |

TABLE 3-continued

Stroke group versus Healthy control group

| Antigen name | Antigen full name | Antigen type | sequence | Immuno-globulin type | up/down regulated |
|---|---|---|---|---|---|
| ERK | Extracellular regulated MAP kinase | peptide | AAEPLQSVLWVKQQRCAVSL | IgG | up | b. The Stroke Group ("2") Versus the AMI Group ("4"):

Table 4 lists 6 antigens that separate the AMI subjects from the Stroke subjects.

TABLE 4

Stroke group ("2") versus AMI ("4") group

| up/down regulated | type | Antigen name |
|---|---|---|
| up | IgG | Tryptophan hydroxylase (peptide 1) |
| up | IgG | Tryptophan hydroxylase (peptide 2) |
| up | IgG | Synaptotagmin1 (peptide) |
| up | IgG | Myelin-Associated Metalloproteinase |
| up | IgM | Bone morphogenic protein 4 |
| up | IgG | D4GDI, GDP-dissociation inhibitor |

Reference is now made to FIG. 4 showing the corresponding graphs of the antibody reactivity levels for each of the antigens. As can be seen, the two peptides of Tryptophan hydroxylase (peptides 1 and 2) are again prominent, as is synaptotagmin 1.

Thus the above described results identified two antigens out of the 740 microarray chip antigens that correctly classified 28 of the 30 specimens of both groups (two errors in the LOO test). These antigens were: 1. TPH 2. Synaptotagmin1.

Reference is now made to Table 5. The numbers provided in the Table indicate the total number of times the antigen microarray chip provided a "4" or a "2" result. This is used in the calculation of the predictive values (positive & negative).

TABLE 5

Stroke group ("2") versus the AMI group ("4")

| I-CHIP | CLINICAL DEFINITION | | | |
|---|---|---|---|---|
| | | 2 | 4 | |
| | 2 | 14 | 1 | 15 |
| | 4 | 1 | 14 | 15 |
| | | 15 | 15 | 30 |
| SENSITIVITY | | | 93.3 | |
| SPECIFICITY | | | 93.3 | |
| PPV | | | 93.3 | |
| NPV | | | 93.3 | |

A permutation test was performed 500 times. The average error rate for the randomization was, as expected, 0.5 and the lowest number of LOO errors obtained was 6, hence the corresponding p-Value for the real result is p<0.002.

It is surprising and unexpected that AMI differs from Stroke significantly in these reactivities. These results implicate that these antigens are specific biomarkers for AMI and therefore, can predict an attack of acute AMI, by comparing pre-AMI sera, and sera taken at the time of attack. The presence of IgG antibodies on the day of an attack implicate these antibodies have been formed by the subject well in advance of the acute episode hence can be considered as biomarkers for AMI subjects.

IV. Conclusions:

An unsupervised analysis using all 740 microarray chip antigens detects a highly correlated subgroup of informative antigens formed by samples appearing in each of the 3 groups.

Both the AMI ("4") and the Stroke ("2") groups can be discriminated from the Healthy control group ("0") with sensitivities and specificities of about 90%.

These results were obtained with ImmunArray's antigen microarray chip.

The discrimination between AMI and stroke is significant since both conditions result from the atherosclerotic process, but in different locations in the vascular system. Thus it is unexpected and highly novel that the antigen chip results can discriminate between different variations of atherosclerosis.

Since the autoantibodies were IgG, it is likely that T-cell reactivity to these antigens is also a factor.

It is herein acknowledged that additional information about the subjects such as gender, subject age, range of ages; time between the event and serum specimen collection; further increases the efficacy of the disclosed method and is well within its scope.

Example 3

It is herein acknowledged that some embodiments of the invention include the use of Luminex xMAP Multiplexing Technology as outlined below. The rapidly growing knowledge base in drug discovery and protein research has placed increased pressure on researchers to quickly gain a greater understanding of protein-protein interactions, cell signaling pathways and markers of metabolic processes. Increasingly, this information is difficult or impractical to obtain using traditional "singleplex" protein detection methods, such as Western blotting. Consequently, several emerging technologies have been introduced that offer "multiplex" detection of proteins from a single biological sample.

MILLIPLEX MAP is based on the Luminex xMAP technology—one of the fastest growing and most respected multiplex technologies offering applications throughout the life-sciences, including clinical diagnostics.

Systems using xMAP technology perform a variety of bioassays including immunoassays on the surface of fluorescent-coded beads known as microspheres, which are then read in a compact analyzer. Using two lasers and high-speed digital-signal processors, the analyzer reads signals on each individual microsphere particle. The capability of adding multiple conjugated beads to each sample results in the ability to obtain multiple results from each sample. Open-architecture xMAP technology enables multiplexing of many types of bioassays reducing time, labor and costs over traditional methods.

It is herein acknowledged that some embodiments of the invention further include the use of Surface Plasmon Resonance Imaging (SPRI) as outlined below.

The excitation of surface plasmons by light is denoted as a surface plasmon resonance (SPR) for planar surfaces or localized surface plasmon resonance (LSPR) for nanometer-sized metallic structures.

This phenomenon is the basis of many standard tools for measuring adsorption of material onto planar metal (typically gold and silver) surfaces or onto the surface of metal nanoparticles. It is behind many color based biosensor applications and different lab-on-a-chip sensors. An aspect of the present invention is the use of SPRI technology in scanning the results of the antigen-antibody reactions, although any scanning method known to persons skilled in the art can be employed.

Example 4

Method for Profiling Autoantibody Reactivities Associated with a Susceptibility to AMI with a Serum Sample of an Individual and Analysing Results Obtained It is herein disclosed a preferred protocol for profiling autoantibody reactivities of AMI susceptibility biomarkers associated with a susceptibility to AMI with a serum or plasma sample of an individual:

- A set of selected antigens detailed above are spotted onto the chip surface, each antigen in a discrete location (address). The antigens may be adsorbed or covalently bound to the chip surface.
- A blood serum or plasma specimen is obtained.
- The specimen is brought into contact with the surface carrying the antigens. A few microliters of the specimen is dropped onto the surface and covered with a cover-slip to spread the serum over the entire surface.
- Incubation under binding conditions is carried out for an hour followed by several washes. Drying is by centrifugation.
- Measuring the results of autoantibody binding. The amount of antibody bound to each antigen-spot is measured. This is done by a common sandwich immunoassay technique, converting the amount of bound antibody into a fluorescent signal using a fluorescently labeled second antibody, specific for human immunoglobulin type (IgG, IgM etc.). This is done as for the serum incubation step (use coverslip, incubate, wash).
- The chip is scanned in a system that produces a fluorescent image of the chip surface. A laser scanner is used in some embodiments. In other embodiments camera based systems are used.
- The image is then analyzed.

Reference is now made to the disclosed method of recognizing the development of an Acute Myocardial Infarction (AMI) process in an individual, wherein the method comprises steps of: (a) profiling specific antibody reactivities or biomarkers associated with AMI susceptibility, and, (b) analysing results obtained. The profiling step comprises the steps of: (i) attaching a set of defined antigens to a substrate; (ii) obtaining a biological fluid derived specimen from an individual, the specimen containing a specific antibody repertoire; and, (iii) binding the antibodies of the biological fluid specimen to the attached antigens thereby forming bound antibody antigen complexes.

Reference is now made to the aforementioned method, wherein the profiling further comprises the steps of obtaining the defined antigens characterized by association with a variety of conditions selected from a group consisting of inflammation, angiogenesis, apoptosis or any other condition involving immune regulation or any combination thereof.

Reference is now made to the aforementioned method, wherein the profiling further comprises the steps of selecting the biological fluid derived specimen from a group consisting of plasma, serum, blood, cerebrospinal fluid, synovial fluid, sputum, saliva, tears, lymph specimen, or any other biological fluid known in the art.

Reference is now made to the aforementioned method, wherein the profiling further comprises steps of selecting the substrate from a group consisting of microarray chip, microarray wafers, microarray strips, ELISA microwells, multiplex beads or any substrate known in the relevant art.

It is herein further disclosed that the aforementioned method, further comprises the steps of selecting the antigens from a group consisting of protein, polypeptide, peptide, nucleic acids, lipids, glycosylated molecules, polypeptides with modifications, polysaccharides or any other biological molecule known in the art.

It is herein further disclosed that the aforementioned method, further comprises the steps of defining the antibody reactivities as IgG, IgM, IgA, IgE antibody isotypes or more specific sub-isotypes of the antibodies.

Reference is now made to the aforementioned method, wherein the analyzing results obtained further comprises the steps of measuring the bound antibody complexes.

Reference is now made to the aforementioned method, wherein the measuring step additionally comprises steps of labeling the bound antibody complexes.

Reference is now made to the aforementioned method, wherein the labeling further comprises the steps of selecting a labeling signal from a group consisting of fluorescent, chemiluminescent, absorptive, electronic, radioactive, paramagnetic or any labeling signal known in the art, or combination thereof.

Reference is now made to the aforementioned method, wherein the labeling step additionally comprises steps of contacting the bound antibody complexes with labeled mixture of secondary antibodies specific for human immunoglobulin types so as to obtain labeled bound antibody antigen complexes.

Reference is now made to the aforementioned method, wherein the analyzing step additionally comprises steps of: (a) scanning the signal produced by the bound antibody complexes so as to form a reactivity matrix; (b) measuring the intensity of the signal; (c) generating and recording results of data associated with the intensity of the signal; (d) producing the results in the form of a signature, profile, set, pattern or matrix characteristic to the individual; (e) comparing the results with a databank containing data concerning the antibody reactivities in populations susceptible to AMI thereby identifying the development of an Acute Myocardial Infarction (AMI) process in the individual.

Reference is now made to the aforementioned method, wherein the measuring and scanning steps are selected from a group consisting of Surface Plasmon Resonance (SPR), ellipsometry, laser scanning, light detecting, photon detecting via a photon multiplier, photographing with a digital camera based system or video system, radiation counting, fluorescence detecting, electronic, magnetic detecting or any other technique known in the art or combination thereof.

Reference is now made to the aforementioned method, wherein the analyzing step further comprises the steps of defining the reactivity as a relative intensity signal of a specific bound antibody as compared to its intensity signal in healthy control individuals.

Reference is now made to the aforementioned method, wherein the analyzing step further comprises the steps of defining the reactivity as a relative intensity signal of a specific bound antibody as compared to its intensity signal in individuals who have had a stroke event.

Reference is now made to the aforementioned method, wherein the analyzing step further comprises the steps of identifying a set of informative antigens possessing higher or a lower intensity reactivity matrix signals as compared to the intensity signals of the antibodies in healthy control individuals.

Reference is now made to the aforementioned method, wherein the analyzing step further comprises the steps of identifying a set of informative antigens possessing higher or a lower intensity reactivity matrix signals as compared to the intensity signals of the antibodies in individuals who have had a stroke event.

Reference is now made to the aforementioned method, wherein the method further comprises steps of: (a) obtaining the antigens attached to the substrate; (b) packaging the substrate attached antigens in a kit containing instructions; and, (c) following the steps according to the instructions.

The current invention further discloses a set of informative antigens useful for recognizing the development of an Acute Myocardial Infarction (AMI) process in an individual. According to certain embodiments of the present invention, some of the herein disclosed informative antigens are specific peptides. The aforementioned set of antigens is selected from a group consisting of Brain-1 oligo-dendrocyte transcription factor, Synaptotagmin 1, Tryptophan hydroxylase peptide 1, Tryptophan hydroxylase peptide 2, BSP (Brain specific protein), myelin associated glycoprotein, Fibronectin, Caspase 3, Myelin-associated metalloproteinase, CD68, Bone morphogenic protein 4 and D4GDI (GDP-dissociation inhibitor), the antibody reactivities are profiled by: (a) profiling means for profiling specific antibody reactivities or biomarkers associated with AMI susceptibility, and, (b) analyzing means for analyzing results obtained. The aforementioned profiling means further comprises steps of: (i) attaching means for attaching a set of defined antigens to a substrate; (ii) a biological fluid derived specimen from an individual, the specimen containing a specific antibody repertoire; and, (iii) binding means for binding the antibodies of the biological fluid specimen to the attached antigens thereby forming bound antibody antigen complexes.

It is the core of the invention that the antigens are further characterised by their specific antibody reactivity with human antibodies associated with susceptibility to AMI.

Reference is now made to the aforementioned set of informative antigens, wherein the defined antigens characterized by association with a variety of conditions selected from a group consisting of inflammation, angiogenesis, apoptosis or any other condition involving immune regulation or any combination thereof.

Reference is now made to the aforementioned set of informative antigens, wherein the defined antigens are attached to a substrate selected from a group consisting of microarray chip, microarray wafers, microarray strips, ELISA microwells, multiplex beads or any substrate known in the relevant art.

Reference is now made to the aforementioned set of informative antigens; wherein the defined antigens are selected form a group consisting of protein, polypeptide, peptide, nucleic acids, lipids, glycosylated molecules, polypeptides with modifications, polysaccharides or any other biological molecule known in the art.

Reference is now made to the aforementioned set of informative antigens, wherein the antigens are further characterized by their specific capability to discriminate between the development of an AMI process in an individual and a healthy control individual.

Reference is now made to the aforementioned set of informative antigens, wherein the antigens are further characterized by their specific capability to discriminate between the development of an AMI process in an individual and an individual who have had a stroke event.

Reference is now made to the aforementioned set of informative antigens, wherein the human antibodies are derived from a biological fluid specimen selected from a group consisting of plasma, serum, blood, cerebrospinal fluid, synovial fluid, sputum, saliva, tears, lymph specimen, or any biological fluid known in the art.

Reference is now made to the aforementioned set of informative antigens, wherein the antibody reactivities are defined as IgG, IgM, IgA, IgE antibody isotypes or more specific sub-isotypes of the antibodies.

Reference is now made to the aforementioned set of informative antigens, wherein the specific antibody reactivity is analyzable by using measuring means.

Reference is now made to the aforementioned set of informative antigens, wherein the specific antibody reactivity is analyzable by using labeling means.

Reference is now made to the aforementioned set of informative antigens, wherein the labeling means is adapted to label the human antibodies with a mixture of secondary antibodies specific for human immunoglobulin types to form a reactivity matrix.

Reference is now made to the aforementioned set of informative antigens, wherein the labeling means comprises labeling signal selected form a group consisting of fluorescent, chemiluminescent, absorptive, electronic, radioactive, paramagnetic or any labeling signal known in the art, or combination thereof.

Reference is now made to the aforementioned set of informative antigens, wherein the specific antibody reactivity is further analyzable by: (a) using a scanning means for scanning the reactivity matrix signal; (b) using a measuring means for measuring the intensity of the signal; (c) using generating and recording means for generating and recording results associated with the reactivity matrix signal; (d) using producing means for producing the results in the form of a signature, profile, set, pattern or matrix characteristic to the individual; and, (e) using means for comparing the results with a databank containing data concerning the antibody reactivities in populations susceptible to AMI, thereby identifying the development of an Acute Myocardial Infarction (AMI) process in the individual.

Reference is now made to the aforementioned set of informative antigens, wherein the measuring and scanning means are selected from a group consisting of Surface Plasmon Resonance (SPR), ellipsometry, laser scanning, light detecting, photon detecting via a photon multiplier, photographing with a digital camera based system or video system, radiation counting, fluorescence detecting, electronic, magnetic detecting or any other technique known in the art or combination thereof.

Reference is now made to the aforementioned set of informative antigens, wherein the reactivity is defined as a relative intensity of a specific antibody bound antigen as compared to its intensity signal in healthy control individuals.

Reference is now made to the aforementioned set of informative antigens, wherein the reactivity is defined as a relative intensity of a specific antibody bound antigen as compared to its intensity signal in individuals who have had a stroke event.

Reference is now made to the aforementioned set of informative antigens, wherein the reactivity is further defined as a set of informative antigens possessing a higher or a lower intensity reactivity signals as compared to the intensity signals of the antigens in the healthy control individuals.

Reference is now made to the aforementioned set of informative antigens, wherein the reactivity is further defined as a set of informative antigens possessing a higher or a lower intensity reactivity signals as compared to the intensity signals of the antigens in individuals who have had a stroke event.

The current invention further discloses a reactivity matrix useful for recognizing the development of an Acute Myocardial Infarction (AMI) process in an individual, comprising at least one substrate embedded with defined antigens. According to certain embodiments of the present invention, some of the herein disclosed defined antigens are specific peptides. The aforementioned antigens are selected from a group consisting of Brain-1 oligo-dendrocyte transcription factor, Synaptotagmin 1, Tryptophan hydroxylase peptide 1, Tryptophan hydroxylase peptide 2, BSP (Brain specific protein), myelin associated glycoprotein, Fibronectin, Caspase 3, Myelin-associated metalloproteinase, CD68, Bone morphogenic protein 4 and D4GDI (GDP-dissociation inhibitor), wherein the antigens are further characterised by their specific antibody reactivity with human specimen containing antibodies associated with susceptibility to AMI.

Reference is now made to the aforementioned reactivity matrix, wherein the antigens characterized by association with a variety of conditions selected from a group consisting of inflammation, angiogenesis, apoptosis or any other condition involving immune regulation or combination thereof.

Reference is now made to the aforementioned reactivity matrix, wherein the human antibodies are derived from a biological fluid specimen selected from a group consisting of plasma, serum, blood, cerebrospinal fluid, synovial fluid, sputum, saliva, tears, lymph specimen, or any biological fluid known in the art.

Reference is now made to the aforementioned reactivity matrix, wherein the antigens are attached to a substrate selected from a group consisting of microarray chip, microarray wafers, microarray strips, ELISA microwells, multiplex beads or any substrate known in the relevant art.

Reference is now made to the aforementioned reactivity matrix, wherein the antigens are selected form a group consisting of protein, polypeptide, peptide, nucleic acids, lipids, glycosylated molecules, polypeptides with modifications, polysaccharides or any other biological molecule known in the art.

Reference is now made to the aforementioned reactivity matrix, wherein the antibody reactivities are defined as IgG, IgM, IgA, IgE antibody isotypes or as more specific sub-isotypes of the antibodies.

Reference is now made to the aforementioned reactivity matrix, wherein the specific antibody reactivity is analyzable by using measuring means.

Reference is now made to the aforementioned reactivity matrix, wherein the specific antibody reactivity is analyzable by using labeling means.

Reference is now made to the aforementioned reactivity matrix, wherein the labeling means is adapted to label the human antibodies with a mixture of secondary antibodies specific for human immunoglobulin types to form a reactivity matrix.

Reference is now made to the aforementioned reactivity matrix, wherein the labeling means comprises labeling signal selected form a group consisting of fluorescent, chemiluminescent, absorptive, electronic, radioactive, paramagnetic or any labeling signal known in the art, or combination thereof.

Reference is now made to the aforementioned reactivity matrix, wherein the specific antibody reactivity is further analyzable by: (a) using a scanning means for scanning the reactivity matrix signal; (b) using a measuring means for measuring the intensity of the signal; (c) using generating and recording means for generating and recording results associated with the reactivity matrix signal; (d) using producing means for producing the results in the form of a signature, profile, set, pattern or matrix characteristic to the individual; and, (e) using means for comparing the results with a databank containing data concerning the antibody reactivities in populations susceptible to AMI, thereby identifying the development of an Acute Myocardial Infarction (AMI) process in the individual.

Reference is now made to the aforementioned reactivity matrix, wherein the measuring and scanning means are selected from a group consisting of Surface Plasmon Resonance (SPR), ellipsometry, laser scanning, light detecting, photon detecting via a photon multiplier, photographing with a digital camera based system or video system, radiation counting, fluorescence detecting, electronic, magnetic detecting or any other technique known in the art or combination thereof.

Reference is now made to the aforementioned reactivity matrix, wherein the reactivity is defined as a relative intensity of a specific antibody bound antigen as compared to its intensity signal in healthy control individuals.

Reference is now made to the aforementioned reactivity matrix, wherein the reactivity is defined as a relative intensity of a specific antibody bound antigen as compared to its intensity signal in individuals who have had a stroke event.

Reference is now made to the aforementioned reactivity matrix, wherein the reactivity is further defined as a set of informative antigens possessing a higher or a lower intensity reactivity signals as compared to the intensity signals of the antigens in the healthy control individuals.

Reference is now made to the aforementioned reactivity matrix, wherein the reactivity is further defined as a set of informative antigens possessing a higher or a lower intensity reactivity signals as compared to the intensity signals of the antigens in individuals who have had a stroke event.

The current invention further discloses a system for recognizing the development of an Acute Myocardial Infarction (AMI) process in an individual. The aforementioned system comprising: (a) a substrate embedded with antigens; (b) biological fluid derived specimen containing a specific antibody repertoire; (c) means for physically contacting the specimen with the surface of the substrate; (d) means for binding the antibodies of the specimen to the antigens embedded in the substrate so as to form bound antibody antigen complexes; (e) a measuring device for quantifying the intensity signal of the bound antibodies; and, (f) a data processor for producing the intensity signals in the form of a signature, profile, set, pattern or matrix characteristic to the individual. It is within the core of the invention that some of the herein disclosed antigens are specific peptides. The aforementioned antigens are selected from a group consisting of Brain-1 oligo-dendrocyte transcription factor, Synaptotagmin 1, Tryptophan hydroxylase peptide 1, Tryptophan hydroxylase peptide 2, BSP (Brain specific protein), myelin associated glycoprotein, Fibronectin, Caspase 3, Myelin-associated metalloproteinase, CD68, Bone morphogenic protein 4 and D4GDI (GDP-dissociation inhibitor), further wherein the antigens are characterised by their specific reactivity with the specimen containing the antibodies associated with susceptibility to AMI, when bound under defined conditions.

Reference is now made to the aforementioned system, wherein the antigens characterized by association with a variety of conditions selected from a group consisting of inflammation, angiogenesis, apoptosis or any other condition involving immune regulation or combination thereof.

Reference is now made to the aforementioned system, wherein the human antibodies are derived from a biological fluid specimen selected from a group consisting of plasma, serum, blood, cerebrospinal fluid, synovial fluid, sputum, saliva, tears, lymph specimen, or any biological fluid known in the art.

Reference is now made to the aforementioned system, wherein the antigens are attached to a substrate selected from a group consisting of microarray chip, microarray wafers, microarray strips, ELISA microwells, multiplex beads or any substrate known in the relevant art.

Reference is now made to the aforementioned system, wherein the antigens are selected form a group consisting of protein, polypeptide, peptide, nucleic acid, lipid, glycosylated molecules, polypeptides with modifications, polysaccharides or any other biological molecule known in the art.

Reference is now made to the aforementioned system, wherein the antibody reactivities are defined as IgG, IgM, IgA, IgE antibody isotypes or as more specific sub-isotypes of the antibodies.

Reference is now made to the aforementioned system, wherein the specific antibody reactivity is analyzable by using measuring means.

Reference is now made to the aforementioned system, wherein the specific antibody reactivity is analyzable by using labeling means.

Reference is now made to the aforementioned system, wherein the labeling means is adapted to label the human antibodies with a mixture of secondary antibodies specific for human immunoglobulin types to form a reactivity matrix.

Reference is now made to the aforementioned system, wherein the labeling means comprises labeling signal selected form a group consisting of fluorescent, chemiluminescent, absorptive, electronic, radioactive, paramagnetic or any labeling signal known in the art, or combination thereof.

Reference is now made to the aforementioned system, wherein the specific antibody reactivity is further analyzable by: (a) using a scanning means for scanning the reactivity matrix signal; (b) using a measuring means for measuring the intensity of the signal; (c) using generating and recording means for generating and recording results associated with the reactivity matrix signal; (d) using producing means for producing the results in the form of a signature, profile, set, pattern or matrix characteristic to the individual; and, (e) using means for comparing the results with a databank containing data concerning the antibody reactivities in populations susceptible to AMI, thereby identifying the development of an Acute Myocardial Infarction (AMI) process in the individual.

Reference is now made to the aforementioned system, wherein the measuring and scanning means are selected from a group consisting of Surface Plasmon Resonance (SPR), ellipsometry, laser scanning, light detecting, photon detecting via a photon multiplier, photographing with a digital camera based system or video system, radiation counting, fluorescence detecting, electronic, magnetic detecting or any other technique known in the art or combination thereof.

Reference is now made to the aforementioned system, wherein the reactivity is defined as a relative intensity signal of a specific antibody bound antigen as compared to its intensity signal in healthy control individuals.

Reference is now made to the aforementioned system, wherein the reactivity is defined as a relative intensity signal of a specific antibody bound antigen as compared to its intensity signal in individuals who have had a stroke event.

Reference is now made to the aforementioned system, wherein the reactivity is further defined as a set of informative antigens possessing a higher or a lower intensity reactivity signals as compared to the intensity signals of the antigens in the healthy control individuals.

Reference is now made to the aforementioned system, wherein the reactivity is further defined as a set of informative antigens possessing a higher or a lower intensity reactivity signals as compared to the intensity signals of the antigens in individuals who have had a stroke event.

The current invention further discloses a kit useful for recognizing the development of an Acute Myocardial Infarction (AMI) process in an individual. The aforementioned kit comprising: (a) a set of antigens selected from a group consisting of Brain-1 oligo-dendrocyte transcription factor, Synaptotagmin 1, Tryptophan hydroxylase peptide 1, Tryptophan hydroxylase peptide 2, BSP (Brain specific protein), myelin associated glycoprotein, Fibronectin, Caspase 3, Myelin-associated metalloproteinase, CD68, Bone morphogenic protein 4 and D4GDI (GDP-dissociation inhibitor) attached to a substrate, wherein the antigens are further characterised by their specific ability to form bound antibody antigen reactivity complexes with human specimen containing antibodies associated with susceptibility to AMI; (b) a mixture of secondary labeled antibodies specific for human immunoglobulin types; (c) components or solutions useful for reacting the antigens with the antibodies of the specimen; (d) components or solutions useful for reacting the antigen antibody complexes with the secondary labeled antibodies; and, (e) instructions for reacting the antigens with the components and the complexes with the secondary antibodies in vitro so as to obtain results useful for identifying an Acute Myocardial Infarction (AMI) process in an individual.

Reference is now made to the aforementioned kit, wherein the antigens characterized by association with a variety of conditions selected from a group consisting of inflammation, angiogenesis, apoptosis or any other condition involving immune regulation or combination thereof.

Reference is now made to the aforementioned kit, wherein the human antibodies are derived from a biological fluid specimen selected from a group consisting of plasma, serum, blood, cerebrospinal fluid, synovial fluid, sputum, saliva, tears, lymph specimen, or any biological fluid known in the art.

Reference is now made to the aforementioned kit, wherein the antigens are attached to a substrate selected from a group consisting of microarray chip, microarray wafers, microarray strips, ELISA microwells, multiplex beads or any substrate known in the relevant art.

Reference is now made to the aforementioned kit, wherein the antigens are selected form a group consisting of protein, polypeptide, peptide, nucleic acid, lipid, glycosylated molecules, polypeptides with modifications, polysaccharides or any other biological molecule known in the art.

Reference is now made to the aforementioned kit, wherein the antibody reactivities are defined as IgG, IgM, IgA, IgE antibody isotypes or as more specific sub-isotypes of the antibodies.

Reference is now made to the aforementioned kit, wherein the specific antibody reactivity is analyzable by using measuring means.

Reference is now made to the aforementioned kit, wherein the specific antibody reactivity is analyzable by using labeling means.

Reference is now made to the aforementioned kit, wherein the labeling means are adapted to label the human antibodies with a mixture of secondary antibodies specific for human immunoglobulin types to form a reactivity matrix.

Reference is now made to the aforementioned kit, wherein the labeling means comprises labeling signal selected form a group consisting of fluorescent, chemiluminescent, absorptive, electronic, radioactive, paramagnetic or any labeling signal known in the art, or combination thereof.

Reference is now made to the aforementioned kit, wherein the specific antibody reactivity is further analyzable by: (a) using a scanning means for scanning the reactivity matrix signal; (b) using a measuring means for measuring the intensity of the signal; (c) using generating and recording means for generating and recording results associated with the reactivity matrix signal; (d) using producing means for producing the results in the form of a signature, profile, set, pattern or matrix characteristic to the individual; and, (e) using means for comparing the results with a databank containing data concerning the antibody reactivities in populations susceptible to AMI, thereby identifying the development of an Acute Myocardial Infarction (AMI) process in the individual.

Reference is now made to the aforementioned kit, wherein the measuring and scanning means are selected from a group consisting of Surface Plasmon Resonance (SPR), ellipsometry, laser scanning, light detecting, photon detecting via a photon multiplier, photographing with a digital camera based system or video system, radiation counting, fluorescence detecting, electronic, magnetic detecting or any other technique known in the art or combination thereof.

Reference is now made to the aforementioned kit, wherein the reactivity is defined as a relative intensity of a specific antibody bound antigen as compared to its intensity signal in healthy control individuals.

Reference is now made to the aforementioned kit, wherein the reactivity is defined as a relative intensity of a specific antibody bound antigen as compared to its intensity signal in individuals who have had a stroke event.

Reference is now made to the aforementioned kit, wherein the reactivity is further defined as a set of informative antigens possessing a higher or a lower intensity reactivity signals as compared to the intensity signals of the antigens in the healthy control individuals.

Reference is now made to the aforementioned kit, wherein the reactivity is further defined as a set of informative antigens possessing a higher or a lower intensity reactivity signals as compared to the intensity signals of the antigens in individuals who have had a stroke event.

The current invention further discloses a method for arresting the development of an AMI process in a patient, wherein the method comprising steps of: (a) profiling the specific antibody reactivities or biomarkers associated with AMI susceptibility, (b) determining the specific AMI associated antigens bound by the antibody repertoires of the individuals specimens; (c) designing a drug comprising at least one of the specific antigens or at least one epitope of the specific antigens; and, (d) administering the drug to the patient thereby arresting the development of an AMI process in a patient.

It is within the scope of the invention that the profiling step comprises steps of: (i) attaching a set of defined antigens to a substrate; (ii) obtaining biological fluid derived specimens from a plurality of individuals in a population, each of the specimens containing their specific antibody repertoire; (iii) binding the antibody repertoire of each of the specimens to the attached antigens thereby forming bound antibody antigen complexes; and, (iv) analysing results obtained.

The current invention further discloses a method for screening for candidate drugs for arresting the development of an AMI process, in a patient. The aforementioned method comprising the steps of: (a) profiling the specific antibody reactivities associated with AMI susceptibility of individuals, (b) determining the specific AMI associated antigens bound by the antibody repertoires of the individuals; and (c) selecting the candidate drugs as appropriate for administration as immunotherapy for arresting the development of an AMI process, in an individual, wherein the candidate drug contains at least one of the specific AMI associated antigens or at least one epitope of the specific antigens. The profiling step further comprising steps of: (i) attaching a set of defined antigens to a substrate; (ii) obtaining biological fluid derived specimens from a plurality of individuals in a population, each of the specimens containing their specific antibody repertoire; (iii) binding the antibody repertoire of each of the specimens to the attached antigens thereby forming antibody antigen complexes; and, (iv) analysing results obtained.

References

1. Quintana F J, Hagedorn P H, Elizur G, Merbl Y, Domany E and Cohen I R. Functional immunomics: Microarray analysis of IgG autoantibody repertoires predicts the future response of mice to induced diabetes. Proc Natl Acad Sci USA 2004; 101 Suppl 2:14615-21.
2. Merbl Y, Zucker-Toledano M, Quintana F J, Cohen I R. Newborn humans manifest autoantibodies to defined self molecules detected by antigen microarray informatics. J Clin Invest. 2007 March; 117(3):712-8.
3. Cohen I R. (2007). Biomarkers, self-antigens and the immunological homunculus. J Autoimmun., 2007 December; 29(4):246-9.
4. Cohen I R. Real and artificial immune systems: computing the state of the body. Nat Rev Immunol. 2007 July; 7 (7):569-74.
5. Maton, Anthea (1993). Human Biology and Health. Englewood Cliffs, N.J.: Prentice Hall. ISBN 0-13-98 1176-1.
6. United States (1999). "Chronic Disease Overview". United States Government. Retrieved on 2007 Feb. 7.
7. Informational page on cardiovascular disease at Itamar Medical.
8. Rainwater D L, McMahan C A, Malcom G T, Scheer W D, Roheim P S, McGill H C Jr, Strong J P. Lipid and apolipoprotein predictors of atherosclerosis in youth: apolipoprotein concentrations do not materially improve prediction of arterial lesions in PDAY subjects. The PDAY Research Group. Arterioscler Thromb Vasc Biol. 1999; 19: 753-61.
9. Mcgill, H C, Jr., Mcmahan, C A, Zieske, A W et al. Associations of coronary heart disease risk factors with the intermediate lesion of atherosclerosis in youth. The Pathobiological Determinants of Atherosclerosis in Youth (PDAY) Research Group. Arterioscler. Thromb. Vasc. Biol. 2000; 20: 1998-2004.
10. Wang T J, Gona P, Larson M G, Tofler G H, Levy D, Newton-Cheh C, Jacques P F, Rifai N, Selhub J, Robins S J, Benjamin E J, D'Agostino R B, Vasan R S (2006). "Multiple biomarkers for the prediction of first major cardiovascular events and death". N. Engl. J. Med. 355 (25): 2631-9. doi:10.1056/NEJMoa055373. PMID 17182988.
11. Ramachandran Vasan, et al. " ". N. Engl. J. Lack Energy? Maybe It's Your Magnesium Level 12. Comparison of Mechanism and Functional Effects of Magnesium and Statin Pharmaceuticals Andrea Rosanoff, PhD, Mildred S. Seelig, MD. Journal of the American College of Nutrition, Vol. 23, No. 5, 501S-505S (2004).
13. Franco, O, Bonneux, L, de Laet. C, Steyerberg, E, Mackenbach, J (2004). "Franco, O, Bonneux, L, de Laet. C, Steyerberg, E, Mackenbach, J". BMJ. 329: 1447-1450. doi:10.1136/bmj.329.7480.1447. PMID 15604180.
14. Studer M, Briel M, Liemenstoll B, Blass T R, Bucher H C. "Effect of different antilipidemic agents and diets on mortality: a systematic review." Arch. Intern. Med. 2005; 165 (7): 725-730.
15. Cook N R, Cutler J A, Obarzanek E, et al. (2007). "Long term effects of dietary sodium reduction on cardiovascular disease outcomes: observational follow-up of the trials of hypertension prevention (TOHP)". Br Med J 334: 885. doi:10.1136/bmj.39147.604896.55. PMID 17449506.
16. Elliott P, Stamler J, Nichols R, et al. (1996). "Intersalt revisited: further analyses of 24 hour sodium excretion and blood pressure within and across populations. Intersalt Cooperative Research Group". Br Med J 312 (7041): 1249-53. PMID 8634612.
17. Godlee F (2007). "Editor's Choice: Time to talk salt". Br Med J 334 (7599): 0. doi:10.1136/bmj.39196.679537.47.
18. Oral Hygiene and Cardiovascular Disease American Heart Association 19. Real connection between oral health and heart disease University of Michigan Jan. 22, 1999.
20. Vanhecke T E, Miller W M, Franklin B A, Weber J E, McCullough P A. Awareness, knowledge, and perception of heart disease among adolescents. European Journal of Cardiovascular Prevention and Rehabilitation. October, 2006; 13(5): 718-723. ISSN 1741-8267.
21. Andraws R, Berger J S, Brown D L. Effects of antibiotic therapy on outcomes of patients with coronary artery disease. JAMA 2005; 293:2641-7. PMID 15928286.
22. Quintana F J, Merbl Y, Sahar E, Domany E, Cohen I R. Antigen-chip technology for accessing global information about the state of the body. Lupus. 2006; 15(7):428-30.
23. Grabar P. "Self" and "not-self" in immunology. Lancet. 1974 Jun. 29; 1(7870): 1320-2.

APPENDIX I

1. Elias D, Markovits D, Reshef T, van der Zee R, Cohen I R. Induction and therapy of autoimmune diabetes in the non-obese diabetic (NOD/Lt) mouse by a 65-kDa heat shock protein. Proc Natl Acad Sci USA 1990; 87(4):1576-80.
2. Elias D, Reshef T, Birk O S, van der Zee R, Walker M D, Cohen I R. Vaccination against autoimmune mouse diabetes with a T-cell epitope of the human 65-kDa heat shock protein. *Proc Natl Acad Sci USA* 1991; 88(8):3088-91.
3. Cohen I R. Peptide therapy for Type 1 diabetes: the immunological homunculus and the rationale for vaccination. Diabetologia. 2002 October; 45(10):1468-74.
4. Raz I, Elias D, Avron A, Tamir M, Metzger M, Cohen I R. Beta-cell function in new-onset type 1 diabetes and immunomodulation with a heat-shock protein peptide (DiaPep277): a randomised, double-blind, phase II trial. *Lancet* 2001; 358(9295): 1749-53.
5. Huurman V A, van der Meide P E, Duinkerken G, Willemen S, Cohen I R, Elias D, Roep B O. Immunological efficacy of heat shock protein 60 peptide DiaPep277 therapy in clinical type I diabetes. *Clin Exp Immunol.* 2008 June; 152(3):488-97.
6. Andromeda Biotech Announces Successful Phase III Interim Results Of Its Lead Product, DiaPep277 For Type 1 Diabetes 2 Jan. 2009.
7. Andromeda Biotech, a subsidiary of Clal Biotechnology Industries (CBI), focused on the development of innovative treatment for autoimmune diabetes announces positive results following the Phase III interim analysis for the company's lead product, DiaPep277 for the treatment of Type 1 diabetes.

An Independent Data Monitoring Committee (IDMC) carefully evaluated the safety and efficacy of the drug for long-term treatment and re-estimated the sample size needed to demonstrate statistically significant efficacy at the completion of the study.

The Committee reviewed results of 233 patients who completed at least 12 months of therapy and recommended proceeding with the study without any change to the design and continuing the enrolment of patients as planned.

The results show that no significant drug related Adverse Events or Serious Adverse Events were reported, hence there are no safety concerns to continue the study. In addition, a clear treatment effect was observed in different sub-group populations. It was recommended that sub-group analyses (age, insulin intake, HLA and C-peptide baseline level) be included in the final report to confirm the observed effect. The Committee concluded that the current number of patients planned to be recruited into the study is expected to be sufficient to achieve a statistically significant effect at the end of the trial as observed in the Interim Analysis.

"The Interim Analysis represents a critical milestone in the development of a novel and effective treatment to prevent the development and progression of Type 1 diabetes using DiaPep 277," said Prof Itamar Raz, Head of the Diabetes Unit at Hadassah University Hospital who chairs the study Steering Committee. "This is the largest international study being conducted for intervention in newly diagnosed Type 1 diabetes using a product that addresses an unmet clinical need."

Dr. Shlomo Dagan, CEO of Andromeda commented that "The report is an achievement for us in the clinical development process and we look forward to completing patient recruitment during the first half of 2009

What is claimed is:

1. A method of recognizing the development of an Acute Myocardial Infarction (AMI) process in an individual, wherein said method comprises profiling specific antibody reactivities to a set of antigens comprising at least six antigens selected from a group consisting of Brain-1 oligo-dendrocyte transcription factor, Synaptotagmin 1, Tryptophan hydroxylase peptide 1, Tryptophan hydroxylase peptide 2, BSP (Brain specific protein), myelin associated glycoprotein, Fibronectin, Caspase 3, Myelin-associated metalloproteinase, CD68, Bone morphogenic protein 4 and D4GDI (GDP-dissociation inhibitor), said profiling comprising the steps of:
  i. obtaining a biological fluid specimen from the individual, said specimen containing a specific antibody repertoire;
  ii. attaching the set of antigens to a substrate;
  iii. binding said antibodies of said biological fluid specimen to said set of antigens attached to the substrate, thereby forming bound antibody antigen complexes;
  iv. analyzing the results obtained, comprising: 1) measuring the bound antibody antigen complexes by scanning the substrate using a measuring device adapted to a utilize a method selected from the group consisting of: Surface Plasmon Resonance (SPR), ellipsometry, laser scanning, light detecting, photon detecting via a photon multiplier, photographing with a digital camera based system or video system, fluorescence detecting, and combination thereof so as to produce a fluorescent image of the substrate; and 2) comparing to control antibody reactivities;
wherein an AMI process in said individual is indicated by a change in the antibody complexes compared to control, wherein the change in the antibody complexes is characterized by: increased antibody complexes with at least one antigen selected from Brain-1 oligo-dendrocyte transcription factor, Synaptotagmin 1, Tryptophan hydroxylase peptide 1, Tryptophan hydroxylase peptide 2, BSP, myelin associated glycoprotein, Fibronectin, Myelin-associated metalloproteinase, CD68, Bone morphogenic protein 4 and D4GDI, or decreased antibody complex with Caspase 3.

2. The method according to claim 1, wherein said analyzing step additionally comprises the steps of:
  a. scanning the signal produced by said bound antibody complexes so as to form a reactivity matrix;
  b. measuring the intensity of said signal;
  c. generating and recording results of data associated with said intensity of said signal;
  d. producing said results in the form of a signature, profile, set, pattern or matrix characteristic to said individual;
  e. comparing said results with a databank containing data concerning said antibody reactivities in populations susceptible to AMI, thereby identifying the development of an Acute Myocardial Infarction (AMI) process in said individual.

3. The method of claim 1, wherein said substrate is a microarray chip and said measuring comprises scanning the chip in a system that produces a fluorescent image of the chip surface.

4. The method of claim 3 wherein said measuring comprises SPR.

5. The method according to claim 1, wherein said biological fluid specimen is selected from the group consisting of plasma, serum, blood, cerebrospinal fluid, synovial fluid, sputum, saliva, tears and lymph specimen.

6. The method according to claim 1, wherein said substrate is selected from the group consisting of microarray chip, microarray wafers, microarray strips, ELISA microwells and multiplex beads.

7. The method according to claim 1, further comprises the steps of defining said antibody reactivities as IgG, IgM, IgA, IgE antibody isotypes or more specific sub-isotypes of said antibodies.

8. The method according to claim 1, wherein said measuring the bound antibody antigen complexes comprises steps of labeling said bound antibody complexes, said labeling further comprises the steps of selecting a labeling signal from a group consisting of fluorescent, chemiluminescent, absorptive, and combination thereof or wherein said labeling step additionally comprises steps of reacting said bound antibody complexes with labeled mixture of secondary antibodies specific for human immunoglobulin types so as to obtain labeled bound antibody antigen complexes.

9. The method according to claim 1, wherein said analyzing step further comprises the steps of defining said reactivity as a relative intensity signal of a specific bound antibody as compared to its intensity signal in healthy control individuals.

10. The method according to claim 1, wherein said analyzing step further comprises the steps of defining said reactivity as a relative intensity signal of a specific bound antibody as compared to its intensity signal in individuals who have had a stroke event.

11. The method according to claim 1, wherein said analyzing step further comprises the steps of identifying a set of informative antigens possessing higher or a lower intensity reactivity matrix signals as compared to said intensity signals of said antibodies in healthy control individuals or wherein said analyzing step further comprises the steps of identifying a set of informative antigens possessing higher or a lower intensity reactivity matrix signals as compared to said intensity signals of said antibodies in individuals who have had a stroke event.

12. A method for differentiating between the development of a stroke and an AMI process in an individual, wherein said method comprises profiling specific antibody reactivities to a set of antigens comprising Synaptotagmin 1, Tryptophan hydroxylase peptide 1, Tryptophan hydroxylase peptide 2, Myelin-associated metalloproteinase, Bone morphogenic protein 4 and D4GDI, said profiling comprising the steps of:
  i. obtaining a biological fluid specimen from the individual, said specimen containing a specific antibody repertoire;
  ii. attaching the set of antigens to a substrate;
  iii. binding said antibodies of said biological fluid specimen to said set of antigens attached to the substrate, thereby forming bound antibody antigen complexes;
  iv. analyzing the results obtained, comprising: 1) measuring the bound antibody antigen complexes by scanning the substrate using a measuring device adapted to a utilize a method selected from the group consisting of: Surface Plasmon Resonance (SPR), ellipsometry, laser scanning, light detecting, photon detecting via a photon multiplier, photographing with a digital camera based system or video system, fluorescence detecting, and combination thereof so as to produce a fluorescent image of the substrate; and 2) comparing to control antibody reactivities;
wherein an AMI process in said individual is indicated by increased antibody complexes with compared to control individuals who have had a stroke event.

13. A microarray of informative antigens useful for recognizing the development of an Acute Myocardial Infarction (AMI) process in an individual, the informative antigens comprising at least six antigens selected from a group consisting of: Brain-1 oligo-dendrocyte transcription factor, Synaptotagmin 1, Tryptophan hydroxylase peptide 1, Tryptophan hydroxylase peptide 2, BSP (Brain specific protein), myelin associated glycoprotein, Fibronectin, Caspase 3, Myelin-associated metalloproteinase, CD68, Bone morphogenic protein 4 and D4GDI (GDP-dissociation inhibitor) wherein said antigens are further characterized by their specific antibody reactivity with human antibodies associated with susceptibility to AMI, and are embedded within at least one substrate.

14. The microarray of claim 13, wherein said substrate is selected from the group consisting of microarray chip, microarray wafers, microarray strips, ELISA microwells and multiplex beads.

15. The microarray of informative antigens of claim 13, further comprising:
   a. a mixture of secondary labeled antibodies specific for human immunoglobulin types;
   b. components or solutions useful for reacting said antigens with antibodies in a biological fluid specimen obtained from an individual, so as to form antigen antibody complexes;
   c. components or solutions useful for reacting said antigen antibody complexes with said secondary labeled antibodies; and
   d. instructions for reacting said antigens with said components and said complexes with said secondary antibodies in vitro so as to obtain results useful for identifying the AMI process in said individual.

16. The microarray of claim 15, further comprising:
   a. a scanning means for scanning the signal produced by said bound antibody complexes so as to form a reactivity matrix;
   b. a measuring means for measuring said intensity of said signal;
   c. generating and recording means for generating and recording results associated with said reactivity matrix signal;
   d. producing means for producing said results in the form of a signature, profile, set, pattern or matrix characteristic to said individual; and
   e. means for comparing said results with a databank containing data concerning said antibody reactivities in populations susceptible to AMI, thereby identifying the development of the AMI process in said individual.

17. The microarray of claim 13, further comprising:
   a. a measuring device for quantifying the intensity signal of antibodies bound to said informative antigens; and/or,
   b. a data processor for producing said intensity signals in the form of a signature, profile, set, pattern or matrix characteristic to said individual.

18. The microarray of claim 17, wherein said substrate is a microarray chip and said measuring device is adapted to scan the chip producing a fluorescent image of the chip surface.

19. The microarray of claim 18, wherein said measuring device is adapted to Surface Plasmon Resonance (SPR).

* * * * *

SEQUENCE LISTING

<160> NUMBER OF SEQ ID NOS: 6

<210> SEQ ID NO 1
<211> LENGTH: 19
<212> TYPE: PRT
<213> ORGANISM: Homo sapiens

<400> SEQUENCE: 1

Asp Pro Ser Ser Val Lys Met Val Gln Ser Asp Phe Met Gln Gly Ala
1               5                   10                  15

Met Ala Ala

```
<210> SEQ ID NO 2
<211> LENGTH: 20
<212> TYPE: PRT
<213> ORGANISM: Homo sapiens

<400> SEQUENCE: 2

Asn Glu Ser Phe Ser Phe Glu Val Pro Phe Glu Gln Ile Gln Lys Val
1               5                   10                  15

Gln Val Val Val
            20

<210> SEQ ID NO 3
<211> LENGTH: 19
<212> TYPE: PRT
<213> ORGANISM: Homo sapiens

<400> SEQUENCE: 3

Pro Leu Leu Lys Ser His Thr Thr Val Leu Ser Val Asp Ser Pro Asp
1               5                   10                  15

Gln Leu Pro

<210> SEQ ID NO 4
<211> LENGTH: 19
<212> TYPE: PRT
<213> ORGANISM: Homo sapiens

<400> SEQUENCE: 4

Lys Ser Ile Thr Ser Ala Met Asn Glu Leu Arg His Asp Leu Asp Val
1               5                   10                  15

Val Asn Asp

<210> SEQ ID NO 5
<211> LENGTH: 19
<212> TYPE: PRT
<213> ORGANISM: Homo sapiens

<400> SEQUENCE: 5

Thr Val Ser Ile Leu Cys Ser Thr Gln Ser Asn Pro Asp Pro Ile Leu
1               5                   10                  15

Thr Ile Phe

<210> SEQ ID NO 6
<211> LENGTH: 20
<212> TYPE: PRT
<213> ORGANISM: Homo sapiens

<400> SEQUENCE: 6

Met Ala Cys His Lys Ile Pro Val Glu Ala Asp Phe Leu Tyr Ala Tyr
1               5                   10                  15

Ser Thr Ala Pro
            20
```